US011052377B2

(12) United States Patent
Tashita et al.

(10) Patent No.: US 11,052,377 B2
(45) Date of Patent: Jul. 6, 2021

(54) SUPPORTED METAL CATALYST

(71) Applicant: TOYO GOSEI CO., LTD., Chiba (JP)

(72) Inventors: Shin-ya Tashita, Chiba (JP); Takashi Miyazawa, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 266 days.

(21) Appl. No.: 16/082,080

(22) PCT Filed: Mar. 10, 2017

(86) PCT No.: PCT/JP2017/009832
§ 371 (c)(1),
(2) Date: Sep. 4, 2018

(87) PCT Pub. No.: WO2017/155120
PCT Pub. Date: Sep. 14, 2017

(65) Prior Publication Data
US 2020/0290018 A1   Sep. 17, 2020

(30) Foreign Application Priority Data

Mar. 11, 2016 (JP) .............................. JP2016-048122

(51) Int. Cl.
*B01J 23/44* (2006.01)
*B01J 23/10* (2006.01)
*B01J 23/20* (2006.01)
*B01J 27/224* (2006.01)
*B01J 27/236* (2006.01)
*B01J 31/06* (2006.01)
*B01J 31/12* (2006.01)
*B01J 31/26* (2006.01)
*B01J 31/36* (2006.01)
*B01J 37/02* (2006.01)
*C07C 41/30* (2006.01)
*C07C 45/00* (2006.01)
*C07C 45/62* (2006.01)
*C07C 67/343* (2006.01)
*C07C 211/48* (2006.01)
*C07C 253/14* (2006.01)
*C07C 269/06* (2006.01)
*C07D 209/08* (2006.01)
*C07D 239/26* (2006.01)
*C07F 7/08* (2006.01)

(52) U.S. Cl.
CPC ............... *B01J 23/44* (2013.01); *B01J 23/10* (2013.01); *B01J 23/20* (2013.01); *B01J 27/224* (2013.01); *B01J 27/236* (2013.01); *B01J 31/06* (2013.01); *B01J 31/124* (2013.01); *B01J 31/26* (2013.01); *B01J 31/36* (2013.01); *B01J 37/0219* (2013.01); *B01J 37/0221* (2013.01); *C07C 41/30* (2013.01); *C07C 45/004* (2013.01); *C07C 45/62* (2013.01); *C07C 67/343* (2013.01); *C07C 211/48* (2013.01); *C07C 253/14* (2013.01); *C07C 269/06* (2013.01); *C07D 209/08* (2013.01); *C07D 239/26* (2013.01); *C07F 7/081* (2013.01); *B01J 2231/326* (2013.01); *B01J 2231/4205* (2013.01); *B01J 2231/4233* (2013.01); *B01J 2231/4238* (2013.01); *B01J 2231/4255* (2013.01); *B01J 2231/4294* (2013.01); *B01J 2231/44* (2013.01); *B01J 2231/645* (2013.01); *B01J 2531/005* (2013.01)

(58) Field of Classification Search
CPC ........................................................ B01J 23/44
See application file for complete search history.

(56) References Cited

U.S. PATENT DOCUMENTS

| 5,015,716 | A | * | 5/1991 | Togashi | ............... | C08J 3/07 427/213.36 |
|---|---|---|---|---|---|---|
| 2004/0077905 | A1 | | 4/2004 | Kobayashi | | |
| 2004/0254066 | A1 | | 12/2004 | Ramarao | | |
| 2007/0027028 | A1 | | 2/2007 | Pears et al. | | |
| 2008/0076662 | A1 | | 3/2008 | Kobayashi | | |
| 2009/0143607 | A1 | * | 6/2009 | Kobayashi | ............ | C07C 67/303 556/443 |
| 2011/0092740 | A1 | | 4/2011 | Figueras et al. | | |
| 2015/0051357 | A1 | * | 2/2015 | Komati | ............... | C07C 5/09 525/523 |
| 2015/0361021 | A1 | | 12/2015 | Kim et al. | | |

FOREIGN PATENT DOCUMENTS

| JP | H029448 A | 1/1990 |
|---|---|---|
| JP | 2002253972 A | 9/2002 |
| JP | 2004533928 A | 11/2004 |
| JP | 2007502203 A | 2/2007 |
| JP | 2007260659 A | 10/2007 |

(Continued)

OTHER PUBLICATIONS

International Search Report dated May 30, 2017 of corresponding application No. PCT/JP2017/009832; 3 pgs.
J. Am. Chem. Soc., "Catalytic Reduction of Olefins with a Polymer-Supported Rhodium(I) Catalyst", 1971, 93, 3062-3063., 1 pg.
Angew. Chem. Int. Ed., "A Soluble Polymer-Bound Ruthenium Carbene Complex: A Robust and Reusable Catalyst for Ring-Closing Olefin Metathesis", 2000, 39, 3896-3898., 3 pgs.
Sun Jie, et al. "Hydrogen production from ethanol steam reforming at low temperature over Ni/Y2O3 catalyst Effect of hydrogen reduction on the catalysts," Journal of Fuel Chemistry and Technology. Oct. 2004. pp. 590-595. vol. 32, No. 5. English Abstract provided.

(Continued)

*Primary Examiner* — Paul V Ward
(74) *Attorney, Agent, or Firm* — Maier & Maier, PLLC

(57) ABSTRACT

A long-life catalyst which can be easily and inexpensively manufactured and has high activity and suppressed leakage of metal. A catalyst according to some embodiments includes: a substrate; and a first metal atom as a catalytic center. The substrate contains a non-metallic atom and a second metal atom, and the non-metallic atom is any one selected from the group consisting of a group 15 element, a group 16 element and a group 17 element.

17 Claims, 1 Drawing Sheet

(56) References Cited

FOREIGN PATENT DOCUMENTS

| JP | 2011-502759 A | 1/2011 |
|----|---------------|--------|
| JP | 2012206052 A  | 10/2012 |
| JP | 2013031806 A  | 2/2013 |
| JP | 2013-123697 A | 6/2013 |
| JP | 2015520019 A  | 7/2015 |
| JP | 2016-002546 A | 1/2016 |

OTHER PUBLICATIONS

Wang Yonggang et al., "Coal Chemical Technology," China University of Mining and Technology Press. Sep. 30, 2014. pp. 337-340.

"Rare Earth Metal Applications," Compilation Group, Metallurgical Industry Press. Aug. 31, 1975. p. 52.

Peng Dequn, "Study on Co/La2O3 Catalyzed Hydrogen Production by Steam Reforming of Ethanol," Jan. 2008.4 pages.

Chinese Office Action dated Jan. 19, 2021, in connection with corresponding CN Application No. 201780015995.0 (20 pp., including machine-generated English translation).

Office Action dated Mar. 23, 2021 in corresponding Japanese Application No. 2018-504623; 19 pages.

\* cited by examiner

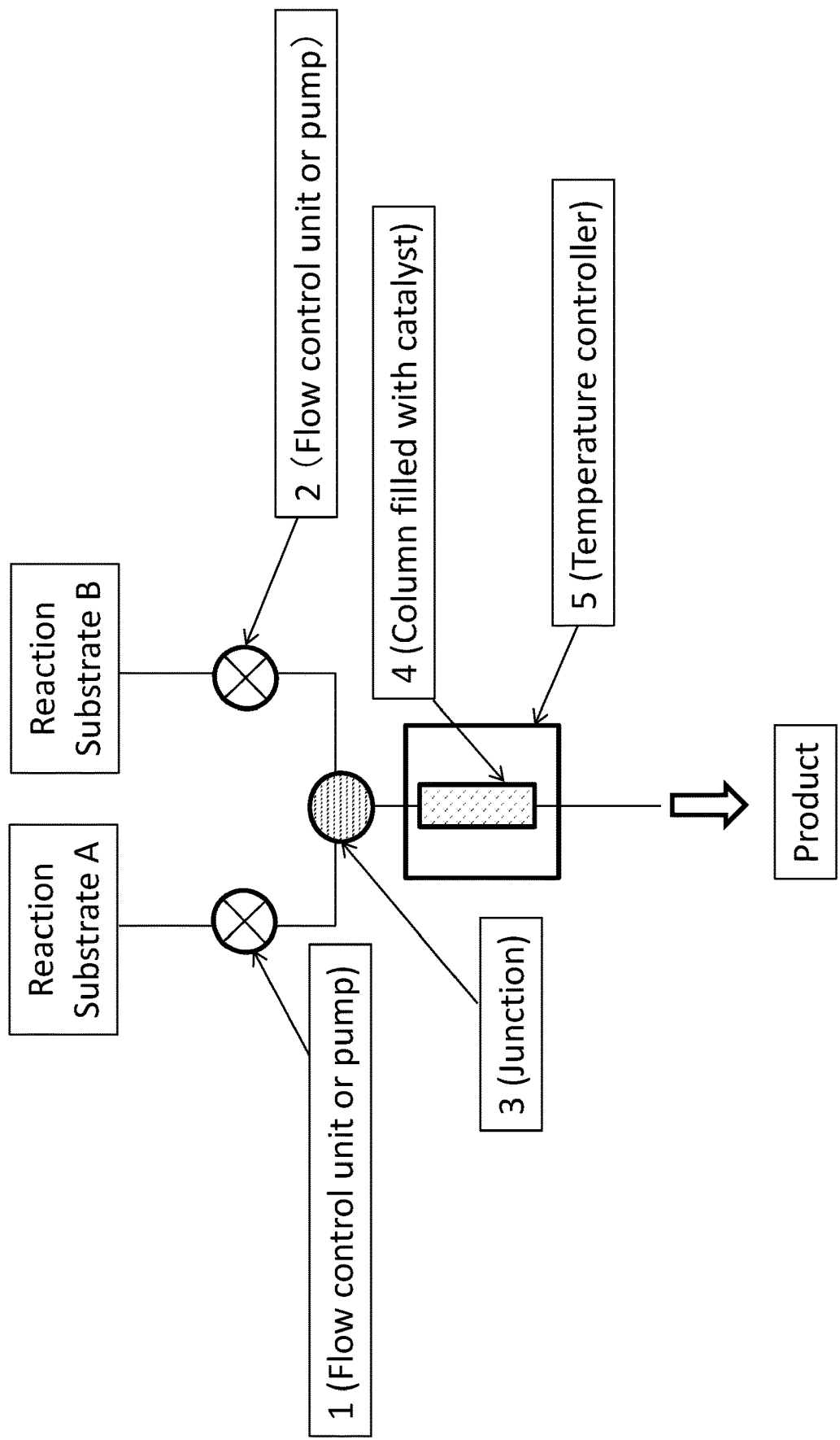

SUPPORTED METAL CATALYST

TECHNICAL FIELD

Some embodiments of the present invention relate to a catalyst containing at least a carrier and a metal atom as a catalytic center supported on the carrier, the catalyst is easy to manufacture and handle, and has excellent durability for the repeated or continuous use.

BACKGROUND ART

Metal is utilized as an important component of catalysts of chemical reactions. Even limited to the field of organic synthesis, the catalysts containing metal, especially transition metal is applied to various kinds of reactions such as reduction reaction, oxidation reaction, hydrometalation reaction, carbon-carbon bond-forming reaction and carbon-nitrogen bond-forming reaction. The catalysts are indispensable elements in the production of industrial products or medicine and agricultural chemicals.

On the other hand, the transition metal includes a rare element such as platinum and palladium that are classified as a rare metal, and is often expensive due to limitations on reserves and production volume. Therefore, from the viewpoint of cost and effective utilization of resources, it is required to recycle the transition metal. For further efficiency improvement, there is also a strong demand for recovering and reusing transition metal catalysts.

As a technique for recovering and reusing the transition metal catalyst or continuously using the transition metal catalyst, it has been tried to immobilize the transition metal catalyst to a polymer or an inorganic material.

For example, it has been reported that a reduction reaction by hydrogenation of a carbon-carbon double bond proceeds with a catalyst in which rhodium is supported as a transition metal on polystyrene introduced a phosphine which may coordinate to rhodium as a substituent (Non-Patent Literature 1).

Further, it has been reported that an olefin metathesis reaction proceeds with a catalyst in which ruthenium is supported on a polyethylene glycol introduced a carbene or a phosphine which may coordinate to ruthenium as a substituent, and by adding diethyl ether as a poor solvent, the polyethylene glycol supported catalyst is recovered (Non-Patent Literature 2).

In the case of using palladium, it has been successful to carry out an allylation reaction and to recover a catalyst by supporting palladium on polystyrene (Patent Literature 1).
Patent Literature1: JP2002-253972
Non-Patent Literature1: J. Am. Chem. Soc., 1971, 93, 3062-3063.
Non-Patent Literature2: Angew. Chem. Int. Ed. 2000, 39, 3896-3898.

SUMMARY

However, introducing a substituent capable of directly bonding to the metal contained in a catalyst to an organic carrier or an inorganic carrier as described above may cause problems such that the synthesize is difficult or that the cost is increased.

Several aspects of the present invention have been made to solve the above problems, and an object of the present invention to provide a long-life catalyst which can be easily and inexpensively manufactured and has high activity or suppressed leakage of metal.

A catalyst according to some embodiments of the present invention comprises: a substrate; and a first metal atom as a catalytic center, wherein the substrate contains a non-metallic atom and a second metal atom, and the non-metallic atom is any one selected from the group consisting of group a 15 element, a group 16 element and a group 17 element.

In the above catalyst, it is preferred that the second metal atom is an alkaline earth metal or a lanthanoid. When the catalyst has such a component, a highly electronegative atom, for example, an atom of group 16 element such as an oxygen atom, an atom of group 15 element such as a nitrogen atom or an atom of group 17 elements such as a fluorine atom contained in a reaction substrate interacts with the substrate, so that an effect such that the reaction is further promoted can be obtained.

In the above catalyst, it is preferred that the catalyst further comprises a polymer containing a plurality of first structural units and a plurality of second structural units, wherein at least a part of the first metal atom and the substrate is covered with the polymer. When the catalyst has such a component, an effect such that leakage of the first metal atom is suppressed can be obtained.

In the above catalyst, it is preferred that: each of the plurality of first structural units has a first constituent atom constituting a main chain of the polymer and a first substituent bonding to the first constituent atom; and a second constituent atom contained in each of the plurality of second structural units bonds to the first constituent atom, where the second constituent atom is different from the first constituent atom, or at least one substituent among all substituents on the second constituent atom is different from the first substituent.

In the above catalyst, it is preferred that the main chain of the polymer does not contain a carbon atom.

In the above catalyst, it is preferred that neither the first constituent atom nor the second constituent atom is a carbon atom.

In the above catalyst, it is preferred that the first constituent atom is a silicon atom.

In the above catalyst, it is preferred that the second constituent atom is an oxygen atom or a nitrogen atom.

In the above catalyst, it is preferred that the first metal atom is any one selected from the group consisting of palladium, platinum, ruthenium, rhodium, silver, gold, copper, nickel, cobalt, iron, chromium, manganese, scandium, indium, lanthanoid (samarium, cerium, lanthanum and the like), technetium, osmium, molybdenum, tungsten, iridium, rhenium, titanium, zirconium, hafnium, tantalum, niobium and vanadium.

In the above catalyst, it is preferred that the first constituent atom is a silicon atom, and the first substituent is at least one of a substituent consisting only of a hydrogen atom, a substituent containing an oxygen atom and a substituent containing a carbon atom.

A method for manufacturing a catalyst according to some embodiments of the present invention comprises: a first step of preparing a first substance containing a first metal atom; a second step of preparing a substrate containing a non-metallic atom and a second metal atom, the non-metallic atom being selected from the group consisting of a group 15 element, a group 16 element and a group 17 elements; and a third step of contacting the first substance and the substrate. Typical examples of the method for manufacturing the catalyst include the manufacturing methods of Examples 31 and 32 described later. Specifically, the first substance and the substrate correspond to sodium tetrachloropalladate (II) and complex oxide of magnesium and lanthanum (MgLaO), respectively.

In the above method for manufacturing catalyst, it is preferred that: a fourth step of preparing a polymer containing a plurality of first structural units and a plurality of second structural units; and a fifth step of reacting the first substance and the polymer.

In the above method for manufacturing catalyst, it is preferred that: at least one first structural unit of the plurality of first structural units has a first constituent atom constituting a main chain of the polymer and a first substituent bonding to the first constituent atom; and a second constituting atom contained in each of the plurality of second structural units bonds to the first constituent atom, where the second constituent atom is different from the first constituent atom, or at least one substituent among all substituents on the second constituent atom is different from the first substituent.

In the above method for manufacturing catalyst, it is preferred that in the second step, a reaction of the first substituent reacts and the first substance occurs.

In the above method for manufacturing catalyst, it is preferred that the first constituent atom is a silicon atom and the first substituent is a hydrogen atom.

In the above method for manufacturing catalyst, it is preferred that an electronegativity of the second constituent atom is higher than an electronegativity of the first constituent atom.

In the above method for manufacturing catalyst, it is preferred that in the second step, the first metal atom is inserted between the silicon atom and the hydrogen atom.

It is preferred that a compound is manufactured by reduction reaction, oxidation reaction, hydrometalation, carbon-carbon bond-forming reaction or carbon-nitrogen bond-forming reaction using the above catalyst.

Some embodiments of the present invention provide a catalyst comprising: a polymer containing a plurality of first structural units and a plurality of second structural units; a metal atom as a catalytic center, wherein: at least a part of the metal atom and the substrate is covered with the polymer; each of the plurality of first structural units has a first constituent atom constituting a main chain of the polymer and a first substituent bonding to the first constituent atom; and a second constituent atom contained in each of the plurality of second structural units bonds to the first constituent atom, where the second constituent atom is different from the first constituent atom, or at least one substituent among all substituents on the second constituent atom is different from the first substituent.

As a result of investigations by the inventors to firmly immobilize a metal atom to a carrier, it is found that the metal is effectively immobilized when several carriers that can be easily synthesized or obtained are used. In addition, when a composition composed of a metal atom and a polymer covering the metal atom is used as a catalyst, various organic synthetic reactions can proceed smoothly, and a target compound can be obtained in high yield or highly selectivity. The catalyst is excellent in durability without leakage of the metal atom after the reaction.

In the above catalyst, it is preferred that the main chain of the polymer does not contain a carbon atom.

In any one of the above catalysts, it is preferred that neither the first constituent atom nor the second constituent atom is a carbon atom.

In any one of the above catalysts, it is preferred that the first constituent atom is a silicon atom.

In any one of the above catalysts, it is preferred that the second constituent atom is an oxygen atom or a nitrogen atom.

In any one of the above catalysts, it is preferred that the metal atom may be any one selected from the group consisting of palladium, platinum, ruthenium, rhodium, silver, gold, copper, nickel, cobalt, iron, chromium, manganese, scandium, indium, lanthanoid (samarium, cerium, lanthanum and the like), technetium, osmium, molybdenum, tungsten, iridium, rhenium, titanium, zirconium, hafnium, tantalum, niobium and vanadium.

In any one of the above catalysts, it is preferred that the first constituent atom is a silicon atom, and the first substituent is at least one of a substituent consisting only of a hydrogen atom, a substituent containing an oxygen atom and a substituent containing a carbon atom.

In any one of the above catalysts, it is preferred that the catalyst further comprises an inorganic member or an organic member.

In any one of the above catalysts, it is preferred that the catalyst further comprises alumina or silicon oxide.

A method for manufacturing a catalyst according to some embodiments of the present invention comprises: a fourth step of preparing a first substance containing a metal atom and a polymer containing a plurality of first structural units and a plurality of second structural units; and a fifth step of reacting the first substance and the polymer, wherein: at least one first structural unit of the plurality of first structural units has a first constituent atom constituting a main chain of the polymer and a first substituent bonding to the first constituent atom; a second constituent atom contained in each of the plurality of second structural units bonds to the first constituent atom, where the second constituent atom is different from the first constituent atom, or at least one substituent among all substituents on the second constituent atom is different from the first substituent; and in the second step, a reaction of the first substituent and the first substance occurs. Examples of the first substance and the polymer in Example 21 described below correspond to palladium(II) acetate and poly(oxydimethylsilylene)(oxymethylhydrosilylene), respectively.

In any one of the above methods for manufacturing catalyst, it is preferred that the first constituent atom is a silicon atom and the first substituent is a hydrogen atom.

In any one of the above methods for manufacturing catalyst, it is preferred that an electronegativity of the second constituent atom is higher than an electronegativity of the first constituent atom.

In any one of the above methods for manufacturing catalyst, it is preferred that in the second step, the metal atom is inserted between the silicon atom and the hydrogen atom.

A method for manufacturing a compound according to some embodiments of the present invention manufactures the compound by reduction reaction, oxidation reaction, hydrometalation, carbon-carbon bond-forming reaction or carbon-nitrogen bond-forming reaction using any one of the above catalyst.

That is, according to the above-described embodiments of the present invention, a highly durable catalyst in which the metal atom is immobilized on the polymer is provided. In addition, a method for manufacturing the catalyst and a method for manufacturing the compound with the catalyst are provided.

A method for manufacturing a composition according to other embodiments of the present invention comprises: a first step of preparing a first substance containing a first metal atom; a second step of reacting a second substance containing a first constituent atom being a group 14 element, a second constituent atom and a third constituent atom with the first substance. It is preferred that in the second step, the first metal atom is oxidized or reduced. In this case, it is preferred that the first constituent atom of the second substance is any one of a silicon atom, a germanium atom, a tin atom and a lead atom.

In the method for manufacturing the above composition, it is preferred that the second step is carried out in a first solvent.

In the method for manufacturing the above composition, it is preferred that the first metal atom is an atom of a transition metal element.

In the method for manufacturing the above composition, it is preferred that the first constituent atom is a silicon atom.

In the second substance, it is preferred that the first constituent atom and the third constituent atom are bonded to each other. Specific examples of the first constituent atom and the third constituent atom are a silicon atom and a hydrogen atom, respectively.

In the second substance of the method for manufacturing the above composition, the first constituent atom may bond to another first constituent atom. In this case, specific examples of the second substance include a substance having a silicon-silicon bond, a germanium-germanium bond, a tin-tin bond or a lead-lead bond, and especially typical example is polysilane, in which a plurality of silicon atoms are linked.

In the method for manufacturing the above composition, it is preferred that the second constituent atom is an oxygen atom or a nitrogen atom.

In the first step of the method for manufacturing the above composition, it is preferred that the first metal atom forms a bond with the first constituent atom or the third constituent atom.

In the method for manufacturing the above composition, it is preferred that the first constituent atom and the third constituent atom are a silicon atom and a hydrogen atom, respectively.

In the method for manufacturing the above composition, it is preferred that the first constituent atom, the second constituent atom and the third constituent atom are a silicon atom, an oxygen atom and a hydrogen atom, respectively.

In the method for manufacturing the above composition, it is preferred that the method further comprises, after the second step, a third step of contacting: a substrate containing a non-metallic atom and a second metal atom; and the first metal atom reduced or oxidized in the first step.

It is preferred that the non-metallic atom is, for example, any one of a group 15 element, a group 16 element and a group 17 element.

It is preferred that the second metal atom is, for example, a metal atom having a valence of 2 or more.

Typical examples of the second metal atom include aluminum, an alkaline earth metal element or lanthanoid.

The most typical example of the non-metallic atom is an oxygen atom.

When the second metal atom is, for example, a metal atom having a valence of 2 or more, a charge density of the second metal atom becomes high, so that when the composition is used as a catalyst, an adsorbent or the like, it may have an effect of facilitating a capture of a reaction substrate.

It is further preferred that, the valence number of the second metal atom is 3 or more.

Preferred examples of the second metal atom having a valence of 3 or more are scandium, yttrium and lanthanoid.

A particularly preferred example among scandium, yttrium and lanthanoid is a lanthanoid such as lanthanum, cerium and lanthanum. Lanthanoid has a small atomic radius due to lanthanoid shrinkage but its charge density is large because its valence is as large as 3. Therefore, when the composition is used as a catalyst, an adsorbent or the like, it may have an effect of facilitating a capture of a reaction substrate.

In the method for manufacturing the above composition, it is preferred that the second substance has an average molecular weight of 500 or more.

In the method for manufacturing the above composition, it is preferred that the second substance has an average molecular weight of 1000 or more. By increasing a molecular weight, insolubility in a solvent increases, so that when the present composition is used as a catalyst or the like of a reaction, it can be easily recovered after the reaction.

Typical examples of the second substance include siloxane and polyethyleneimine.

A siloxane which is a typical example of the second substance may be a siloxane in which a silylene portion and an oxygen atom are alternatively repeated, and the silylene portion having two organic groups which may be different and the oxygen atom bonding to the silylene portion.

A siloxane which is a typical example of the second substance may be a siloxane in which a silylene portion and an oxygen atom are alternatively repeated, the silylene portion having two organic groups which may be different and an oxygen atom, and a part of the silylene portion is preferably replaced by a silylene portion having at least one hydrogen atom.

A siloxane which is a preferred example of the second substance has a silylene portion having an organic group and a hydrogen atom. This is because the bond between the silicon atom and the hydrogen atom is easy to interact with the first metal atom and it is possible to reduce or oxidize the first metal atom.

In particular, when the first metal atom is a transition metal atom such as palladium, platinum, ruthenium and rhodium, the silicon-hydrogen bond is particularly easy to interact, so that the valence of the first metal atom can be rapidly changed.

In the method for manufacturing the above composition, it is preferred that the method further comprises a fourth step of aggregating particles containing the first metal atom.

In the method for manufacturing the above composition, it is preferred that the particles include a cluster generated by reducing or oxidizing the first metal atom in the second step.

In the method for manufacturing the above composition, the aggregation of the particles can be caused by adding a second solvent.

A catalyst composition according to some embodiments of the present invention includes any one of the above catalysts and a member or a balancer.

In the above catalyst composition, the member or the balancer has an effect such as maintaining a form and improving the mechanical strength of the catalyst. When the catalyst composition is used for a flow reaction, it has an effect such as stabilization of pressure and flow rate of a flow reaction system.

Typical examples of the member or the balancer include a compound such as silicon oxide ($SiO_2$), an oxide containing titanium, zirconium, magnesium and aluminum. More specifically, titanium oxide ($TiO_2$), zirconium oxide ($ZrO_2$), magnesium oxide (MgO), alumina ($Al_2O_3$), zeolite and hydrotalcite can be used. A ceramic such as silicon carbide, silicon nitride and boron nitride, and a carbon material such as diamond and carbon fiber can also be used.

BRIEF DESCRIPTION OF DRAWINGS

FIG. 1 describes a schematic diagram of an apparatus in a flow reaction system.

DETAILED DESCRIPTION

Hereinafter, embodiments according to some aspects of the present invention will be described. Various features described in the embodiments described below can be combined with each other. Also, the invention is independently established for each feature.

1. Supported Metal Catalyst

A metal catalyst supported on a substrate or a carrier obtained according to some embodiments of the present invention is composed of a metal as a catalytic center and a substrate or a carrier supporting the metal. Preferably, the substrate or the carrier supporting the metal is an organic member or an inorganic member.

<Substrate>

It is preferred that the substrate or the carrier is a substrate that has a supporting ability to immobilize a metal as a catalytic center and that is stable even under a reaction condition. Any type of a member can be used without limitation, but, for example, an organic member such as polystyrene resin and polyacrylic resin or an inorganic member can be used. As the inorganic member, a metal compound, an activated carbon or the like can be used. As the metal compound, a compound such as silicon oxide ($SiO_2$), an oxide containing titanium, zirconium, magnesium, aluminum or the like can be used. More specifically, a metal oxide such as titanium oxide ($TiO_2$), zirconium oxide ($ZrO_2$), magnesium oxide (MgO), alumina ($Al_2O_3$), zeolite and hydrotalcite are preferred due to the chemical stability and mechanical strength. As a member having the same effect, a ceramic such as silicon carbide, silicon nitride and boron nitride, carbon fiber and the like can also be used. Among the metal oxides, it is particularly preferred to contain an alkaline earth metal or a lanthanoid. When the catalyst has such components, a highly electronegative atom, for example, an atom of group 16 element such as an oxygen atom, an atom of group 15 element such as a nitrogen atom or an atom of group 17 element such as a fluorine atom contained in a reaction substrate interacts with the substrate, so that effects such that a reaction are further promoted can be obtained.

It is preferred that the metal at the catalytic center supported on the substrate is covered with a polymer or a resin. The polymer or the resin may be a homopolymer, composed of repetition of the same structural unit, or a copolymer, having two or more different structural units. Examples of the copolymer include a random copolymer, in which different structural units are randomly bonded, and a block copolymer, in which the same structural unit is repeated, as the copolymer. Preferably, the polymer contains a plurality of first structural units and a plurality of second structural units, wherein: each of the plurality of first structural units has a first atom constituting a main chain of the polymer and a first substituent bonding to the first atom; and a second atom contained in each of the plurality of second structural units bonds to the first atom, where the second atom is different from the first atom, or at least one substituent among all substituents on the second atom is different from the first substituent.

More preferably, each atom in the structural unit and the substituent on the second atom satisfy any one of the following elements (1) to (7). More preferably, at least one other element is simultaneously satisfied. Most preferably, all elements are satisfied.

(1) The main chain of the polymer does not contain a carbon atom.
(2) The first atom is an atom other than an oxygen atom and a nitrogen atom.
(3) The first atom is a silicon atom.
(4) The second atom is an oxygen atom or a nitrogen atom.
(5) The first atom is a silicon atom, and the first substituent is at least one of a substituent consisting only of a hydrogen atom, a substituent containing an oxygen atom and a substituent containing a carbon atom.
(6) The first atom is a silicon atom and the first substituent is a hydrogen atom.
(7) An electronegativity of the second atom is higher than an electronegativity of the first atom.

Typical examples of a polymer for coating according to the present invention include a polymer in which an atom of group 14 element such as a carbon atom or a silicon atom bonds with an atom of group 16 element such as an oxygen atom or a sulfur atom, and a polymer in which an atom of group 14 element such as a silicon atom bonds with an atom of group 15 element such as a nitrogen atom or a phosphorus atom. Typical examples of a polymer for coating according to the present invention include a polymer such as carbosilane, in which different atoms of group 14 elements are bonded, or a polymer in which π electron system is linked through a linking group such as a methylene group. More preferably, the polymer has, on the atom of group 14 element, an organic group such as an alkyl group or an alkoxy group or a hydrogen atom. Specific examples of the polymer include: a polymer in which a main chain is composed of a carbon atom and a hetero atom such as polyethyleneimine, polyester and polymethylene phenylene isocyanate; polysiloxanes such as poly(oxymethylhydrosilylene), poly(oxydimethylsilylene)(oxymethylhydrosilylene), poly(oxydimethylsilylene)(oxydihydrosilylene), poly(oxydimethylsilylene)(oxydiphenylsilylene) and poly(oxymethylphenylsilylene): polysilazanes such as perhydropolysilazane, polydimethylsilazane, poly(dimethylmethyl)silazane, polymethylsilazane, poly(1,1-dimethyl-2-methylpolysilazane), poly(1,1-diphenyl-2-methylpolysilazane), poly(1,1-diphenyl-2-phenylpolysilazane), poly(1-methyl-1-phenyl-2-methylpolysilazane) and poly(poly(1-methyl-1-phenyl-2-phenylpolysilazane); and polysilanes such as poly(methylene)(methylsilylene) and poly(methylene)(dimethylsilylene). These may be synthesized in advance or may be generated in the reaction system during catalyst manufacturing. It is preferred that the polymer contains a silicon atom and has, on the silicon atom, at least one hydrogen atom. The silicon-hydrogen bond interacts with a transition metal such as a palladium ion, a ruthenium ion, a rhodium ion and a platinum ion, and can reduce these metal ions. Depending on the metal, a metal cluster exhibiting catalytic activity may be generated by the reduction.

As an example, referring to a polysiloxane analog in detail, the main chain of the polymer is composed of a silicon atom and an oxygen atom. More specifically, the main chain may be constituted by repetition of a unit derived from a single monomer having the same substituent on the silicon, and may also be constituted by repetition of units derived from two or more kinds of monomers having different substituents on the silicon. In the latter case, particularly, a random copolymer or a block copolymer is selected appropriately according to the desired performance.

The polysiloxane analog preferably has a hydrogen atom as a substituent on the silicon at a certain rate. The rate of hydrogen atom to all substituents on the silicon atom is preferably determined according to a reducing ability required for reducing a target metal atom. When it has the hydrogen atom as a substituent on the silicon atom, it can also act as a reducing agent. In addition, when it has the hydrogen atom as the substituent on the silicon atom, the metal atom is reduced, and at the same time, it is changed into a silanol group by a trace amount of moisture or the like. This silanol group can further undergo dehydration condensation to form a crosslinked structure, which is considered to immobilize and coat the metal more effectively.

It is preferred that an average molecular weight of the polysiloxane analog is typically 500 or more. It is more preferred that the average molecular weight is 1000 or more. It is preferred that a content of hydrogen is 60 g/mol or more. However, if the hydrogen content is too high, hydrogen gas may be generated when reacting with the metal atom, which may be dangerous in operation, so that it is preferably 200 g/mol or less.

The polysiloxane analog such as poly(oxymethylhydrosilylene), poly(oxydimethylsilylene)(oxymethylhydrosilylene) and poly(oxydimethylsilylene)(oxydihydsilylene) can be easily synthesized or inexpensively available and is very stable and easy to handle. Accordingly, when mass manufacturing of the catalyst is carried out using the above-mentioned polysiloxane analog as a metal substrate or the carrier of the metal, it is excellent in that raw materials can be easily available and does not need special facility in consideration of deterioration of the raw materials or the like is not required.

<Metal>

The first metal atom as a catalytic center is preferably a transition metal containing a transition metal element of groups 3 to 13. More preferably, the first metal atom includes palladium, platinum, ruthenium, rhodium, silver, gold, copper, nickel, cobalt, iron, chromium, manganese, technetium, osmium, molybdenum, tungsten, iridium, rhenium, titanium, zirconium, hafnium, tantalum, niobium, vanadium or the like.

In the catalyst, the first metal atom may be present in a state in which the first metal does not bond to a ligand, or may bond to a ligand. For example, in the case of comprising a step of using a reducing agent in the manufacturing of the catalyst, it is considered that palladium, platinum, gold and the like are supported as a zero valent metal cluster having no ligand on the polymer.

In some embodiments of the present invention, examples of a substance containing the first metal atom that can be used for manufacturing the catalyst include those having no bond to an atom of ligands or another element, those having a bond to an atom of ligand or another element, or those having an anionic ligand or a neutral ligand are conceivable. Examples of the other element include: a halogen such as fluorine, chlorine, bromine and iodine; a group 15 element such as nitrogen and phosphorus: a group 16 element such as oxygen and sulfur; and carbon. Examples of the anion include: a halide ion such as fluoride ion, chloride ion, bromide ion and iodide ion; an ion containing carbon atom such as acetate, triflate, mesylate, alkoxide, acetylacetonate, trifluoroacetate, propionate, cyano and hexafluoroacetylacetonate; hydroxide ion; nitrate; sulfonate; and a complex salt or a hydrate thereof. Examples of the neutral ligand include: a ligand containing a group 16 element such as an oxygen atom and a sulfur atom; and a ligand containing a group 15 element such as a phosphorus atom or a nitrogen atom.

As specific examples of the substance containing the first metal atom, bis(2,4-pentanedionato)titanium(IV) oxide, dichlorotitanium diisopropoxide, tetra-n-butyl orthotitanate, tetraethyl orthotitanate, tetraisopropyl orthotitanate, titanium(III) chloride, titanium(IV) chloride, bis(2,4-pentanedionato)vanadium(IV) oxide, vanadium(III) chloride, vanadium (IV) chloride, chromium(III) acetate, chromium(II) chloride, chromium(III) chloride, chromium(III) nitrate, pyridinium chlorochromate, pyridinium dichromate, tris(2,4-pentanedionato)chromium (III), manganese(II) acetate, manganese(III) acetate, manganese(II) chloride, manganese (II) nitrate, manganese(II) sulfate, bis(hexafluoroacetylacetonato)manganese (II), bis(2,4-pentanedionato)manganese (II), tris(2,4-pentanedionato)manganese(III), iron(II) acetate, iron(III) oxalate, iron(II) chloride, iron(III) chloride, iron(III) nitrate, iron(II) sulfate, iron(III) sulfate, ferrocene (II), n-butylferrocene(II), tris(2,4-pentanedionato)iron(III), cobalt(II) acetate, bis(2,4-pentanedionato)cobalt(II), tris(2,4-pentanedionato)cobalt(III), cobalt(II) chloride, cobalt(II) nitrate, nickel(II) acetate, bis(2,4-pentanedionato)nickel(II), nickel(II) chloride, nickel(II) nitrate, nickel(II) oxalate, tetrakis(triphenylphosphine)nickel(0), potassium tetracyanonickelate(II), copper(I) acetate, copper(II) acetate, copper(I) bromide, copper(II) bromide, copper(I) chloride, copper(II) chloride, copper(I) iodide, copper(II) iodide, copper(II) nitrate, copper(II) sulfate, bis(2,4-pentanedionato)copper (II), potassium tetrachlorocuprate(II), zinc(II) acetate, bis(2,4-pentadionato)zinc(II), zinc(II) nitrate, zinc(II) sulfate, tetrakis(2,4-pentanedionato)zirconium(IV), zirconocene(IV) dichloride, zirconium(IV) chloride, zirconium(IV) ethoxide, zirconium(IV) propoxide, zirconium(IV) nitrate, niobium (V) chloride, niobium(V) ethoxide, molybdenum(II) acetate, molybdenum(III) chloride, molybdenum(IV) chloride, molybdenum(V) chloride, bis(2,4-pentanedionato)molybdenum(IV) dioxide, ruthenium(III) chloride, rhodium(II) acetate, rhodium(III) chloride, rhodium(III) nitrate, bis(1,5-cyclooctadiene)-µ,µ'-dichlororhodium, tris(triphenylphosphine)rhodium(I) chloride, palladium(II) acetate, palladium (II) chloride, palladium(II) nitrate, bis(2,4-pentanedionato) palladium(II), tetrakis(triphenylphosphine)palladium(0), potassium tetrachloropalladate(II), silver(I) acetate, silver(I) trifluoromethanesulfonate, silver(I) chloride, silver(I) nitrate, silver(I) sulfate, silver(I) p-toluenesulfonate, cadmium(II) acetate, cadmium(II) chloride, cadmium(II) nitrate, cadmium(II) sulfate, acetylacetonatohafnium(IV), hafnium(IV) chloride, hafnium(IV) ethoxide, hafnium(IV) isopropoxide, hafnocene dichloride, hafnium(IV) trifluoromethanesulfonate, tantalum(V) chloride, tantalum(V) ethoxide, tungsten(IV) chloride, tungsten(IV) ethoxide, hexacarbonyltungsten, tungstic acid, rhenium(III) chloride, rhenium(IV) chloride, rhenium(V) chloride, rhenium pentacarbonylchloride, osmium(III) chloride, iridium(III) chloride, iridium(IV) chloride, platinum(II) chloride, platinum(IV) chloride, potassium hexachloroplatinate(IV), hexachloroplatinic(IV) acid hexahydrate, tetrakis(triphenylphosphine) platinum(0), potassium tetrachloroplatinate(II), gold(I) chloride, gold(III) chloride, gold(III) bromide, potassium tetracyanoaurate(III), tetrachloroauric(III) acid, tetrachloroauric(III) acid tetrahydrate, (triphenylphosphine)gold(I) chloride, mercury(I) acetate, mercury(II) acetate, mercury(I) chloride, mercury(II) chloride, mercury(I) nitrate, mercury (II) nitrate, mercury(I) sulfate, mercury(II) sulfate and the like can be used.

2. Method for Manufacturing Supported Metal Catalyst

A method for manufacturing a supported metal catalyst according to some embodiments of the present invention comprises the steps of: preparing a first substance containing a first metal atom and a substrate or a carrier; and contacting the first substance and the substrate or the carrier. By these steps, the first metal atom is supported on the substrate or the carrier. It is preferred that the substrate or the carrier has a non-metallic atom selected from the group consisting of a group 15 element, a group 16 element and a group 17 element. The method may further comprise, after the above steps, a step of mixing with an inorganic member or an organic member and further supporting a polymer containing a transition metal on the inorganic member or the organic member.

<Mixing>

In the step of contacting the first substance and the substrate or the carrier, a method of directly kneading the first substance and the substrate or the carrier, or a method of mixing with a solvent is conceivable. In the case where the first substance is reacted with a reducing agent to lower the valence of the first metal atom contained in the first substance and to be supported on the substrate or the carrier, it is preferred that the mixing is performed using a solvent.

<Solvent>

In the case where a solvent is used in the above step, the solvent is preferably a solvent which dissolves or disperses the first substance to some extent and does not directly react with the first substance. When the first substance is hydrolyzable, it is preferred to use an organic solvent. Also, when a reducing agent is used, it is preferably an aprotic organic solvent from the view point of reactivity. As examples of the aprotic organic solvent, an ether solvent such as diethyl ether and tetrahydrofuran (THF), an aromatic hydrocarbon such as benzene and toluene, a halogenated hydrocarbon such as dichloromethane and chloroform, or the like is used. Preferably, tetrahydrofuran (THF), toluene or the like is used.

<Reducing Agent>

In the case of reducing the first substance in the manufacturing step of the catalyst, a kind of reducing agent can be appropriately selected, and for example, a metal hydride complex compound or a metal hydride such as lithium aluminum hydride, diisobutylaluminum hydride, sodium borohydride, triphenyltin hydride or tri-n-butyltin hydride; hydrosilanes such as trichlorosilane, trimethylsilane, triethylsilane, trimethoxysilane or triethoxysilane; a borane derivative such as diborane, amine borane complex or alkyl borane; alcohols such as methanol, ethanol or isopropyl alcohol; formic acid and hydrogen gas; a polysiloxane (hydropolysiloxane) having a silicon-hydrogen bond such as poly(oxydimethylsilylene)(oxymethylhydrosilylene) (PMHS) as a polymer; and a polymer having a silicon-silicon bond such as poly(dialkylsilylene) or poly(phenylalkylsilylene) may be used as the reducing agent. In particular, from the view point of cost, safety, environmental influence and the like, sodium borohydride, triethylsilane, hydrogen gas or hydropolysiloxane is preferred. When a polymer is used as the reducing agent, it contributes to immobilization or coating of the first metal atom to the substrate or the carrier, so that the catalyst can be prepared in a short process.

<Conditions for Mixing and Reduction>

When mixing the first substance and a substrate composed of an inorganic member or an organic member or the like in a solvent, the reaction temperature is appropriately set. However, if it needs that the first substance is changed by a chemical reaction such as reduction or oxidation, it is preferred to set, after adding a reaction reagent for chemically changing the first substance, the reaction liquid to a temperature at which the chemical reaction proceeds for a certain period. In this case, it is preferred that the first substance is chemically reacted and then supported on the substrate. Of course, it is also possible to simultaneously add the first substance, the reaction reagent for chemically changing the first substance and the carrier, and to mix. Typically, however, it is easier to control the electronic state and the valence of the first metal atom by providing a step of supporting the first substance after the chemical change as described above.

Further, when it is necessary to cover the substrate with a polymer in a state where the first metal atom contained in the first substance is supported on the substrate, a polymer, a raw material of the polymer or a monomer may be added after supporting the first metal atom on the substrate. When a monomer is used, it is preferred to add a polymerization initiator additionally or that the first metal atom or the substrate functions as a polymerization initiator.

3. Method for Manufacturing Compound Using Supported Metal Catalyst

By using the supported catalyst according to some embodiments of the present invention, various chemical reactions such as a reduction reaction, an oxidation reaction, a hydrometalation, a carbon-carbon bond-forming reaction or a carbon-nitrogen bond-forming reaction smoothly proceed, and the desired product can be obtained with high yield. Furthermore, many of these catalysts can be easily recovered, and only a slight leakage of the metal is observed. For example, by making it possible to use the catalyst repeatedly in this manner, even when expensive noble metals such as palladium, rhodium, platinum or ruthenium must be used as the catalytic center, the manufacturing cost of the target product can be reduced.

<Reduction Reaction>

In manufacturing the supported catalyst according to some embodiments of the present invention, various reduction reactions can be used. Examples of reaction reagents used in the reduction reaction include a metal hydrogen complex compound, a metal hydride, hydrosilanes, which is a compound having a silicon-hydrogen bond, a borane derivative, amines such as hydrazine, and a compound having a silicon-silicon bond such as polysilane can be used. Preferably, alcohols, formic acid, amines, hydrogen gas and the like which are easy to handle and inexpensive are used. More preferably, hydrogen gas which can be easily scaled up and can be used for mass manufacturing is used as the reducing agent. In FIG. 1, a schematic diagram of an apparatus in a flow reaction system is described. According to this apparatus configured so that a reaction substrate and a hydrogen gas are continuously supplied pass through the supported metal catalyst according to some embodiments of the present invention fixed to the flow path, the reduction reaction can be carried out continuously.

By using the supported metal catalyst according to some embodiments of the present invention, a hydrogenation reaction to various unsaturated bonds proceeds under a relatively mild condition. The reaction proceeds under a hydrogen gas atmosphere at about atmospheric pressure, it may also proceed under an atmosphere of a mixed gas with an inert gas such as nitrogen gas or argon gas, and the pressure may be appropriately adjusted.

<Oxidation Reaction>

Various oxidation reactions can be provided by using the supported metal catalysts according to some embodiments of the present invention. An oxygen gas, a peroxide, a hypervalent iodic acid and the like can be used as an oxidizing agent.

By using the supported metal catalyst according to some embodiments of the present invention, Wacker oxidation reaction to various unsaturated bonds proceeds under a relatively mild condition. The reaction proceeds at a reaction temperature of about room temperature, but it is not particularly limited to around room temperature and may be lower temperature or higher temperature. The reaction proceeds under an oxygen gas atmosphere at about atmospheric pressure, the reaction may also proceed under an atmosphere of a mixed gas with an inert gas such as nitrogen gas or argon gas, and the pressure may be appropriately adjusted.

<Carbon-Carbon Bond-Forming Reaction>

By using the supported metal catalyst according to some embodiments of the present invention, it is possible to provide various carbon-carbon bond-forming reactions and to apply to cyclopropanation reaction, ene reaction, pericyclic reaction, aldol reaction, Michael addition, Hosomi-Sakurai reaction, cross coupling reaction, metathesis reaction and the like. Examples of the cross coupling reaction preferably include Heck reaction, Sonogashira coupling reaction, Suzuki-Miyaura coupling reaction, Kumada coupling reaction, Negishi coupling reaction, Tsuji-Trost reaction, Stille coupling reaction and the like.

<Carbon-Nitrogen Bond-Forming Reaction>

By using the supported metal catalyst according to some embodiments of the present invention, it is possible to provide various carbon-nitrogen bond-forming reactions and to apply to a reaction such as Backwald-Hartwig cross coupling reaction, allylation reaction of an amine and the like.

<Hydrometalation>

By using the supported metal catalyst according to some embodiments of the present invention, it is possible to provide various hydrometalation reactions and to apply to a reaction such as hydroboration, hydroalumination, hydrozilconation, hydrostannylation, hydrosilylation and the like.

EXAMPLES

Examples of the supported metal catalyst according to some embodiments of the present invention are described below, but the present invention is not limited thereto.

<Manufacturing of Supported Metal Catalyst>

A method for manufacturing a typical catalyst according to some embodiments of the present invention is described below.

A solution or dispersion containing the first substance and a reducing agent is prepared and stirred for a certain time. Thereafter, an inorganic member or an organic member to be a substrate or a carrier, or a suspension thereof is added to the solution or the dispersion, further stirred and filtered to obtain the catalyst as a powder. Before filtering, a solvent for reprecipitation of the catalyst such as methanol may be added to reprecipitate the catalyst.

In another method, the first substance and the inorganic member or the organic member to be the substrate are mixed in a solvent to contact the first substance and the substrate. Thereby the first metal atom is supported on the substrate. Next, in a state where the first metal atom is supported on the substrate, a reducing agent, a solution or dispersion thereof, if necessary further a polymer or a monomer to be a precursor of a polymer or a solution or dispersion thereof is added, and further stirred and filtered to obtain the catalyst as a powder. Before filtering, a solvent for reprecipitation such as methanol may be added to reprecipitate the catalyst. Details of each are described as Examples 1 to 32 below.

Example 1

A solution of 250 mg of poly(oxydimethylsilylene) (PDMS) (Shin-Etsu Silicone Co., catalog number: KF-96) in THF is prepared, 6 mg of palladium(II) acetate (Pd(OAc)$_2$) is added thereto, and the mixture is stirred at the 0° C. for 55 minutes under a hydrogen gas (H$_2$) atmosphere. Subsequently, 1.25 g of complex oxide of magnesium and lanthanum (MgLaO) is added to the mixture and stirred at room temperature for 25 minutes. Methanol (MeOH) is added thereto and the mixture is further stirred for 5 minutes to reprecipitate, followed by suction filtration and washing with methanol twice to obtain a palladium catalyst supported on poly(oxydimethylsilylene) and MgLaO (PSiO—Pd/MgLaO) as a powder. Note that the polymer containing the plurality of first structural units and the plurality of second structural units corresponds to poly(oxydimethylsilylene) in this example, and for example, a dimethylsilylene portion and an oxygen atom bonding to the dimethylsilylene portion correspond to the plurality of first structural units and the plurality of second structural units, respectively.

[Chem. 1]

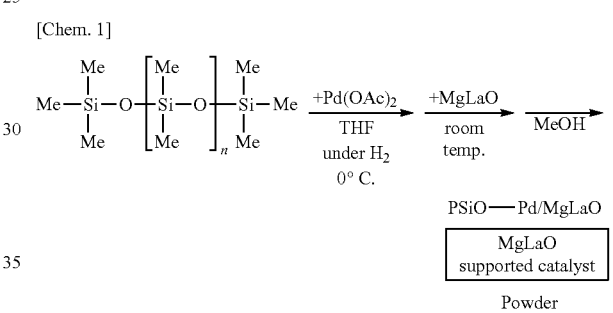

Example 2

A solution of 250 mg of poly(oxydimethylsilylene) in THF is prepared, 6 mg of palladium(II) nitrate (Pd(NO$_3$)$_2$) is added thereto, and the mixture is stirred at the 0° C. for 55 minutes under a hydrogen gas atmosphere. Subsequently, 1.25 g of cerium oxide (CeO$_2$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and cerium oxide (PSiO—Pd/CeO$_2$) as a powder.

[Chem. 2]

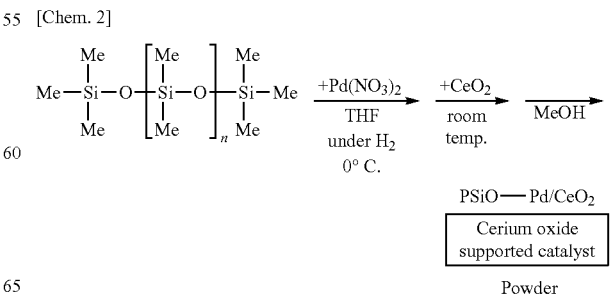

Example 3

A solution of 250 mg of polyethyleneimine (PEI) (Wako Pure Chemical Industries, catalog number: 167-1195) in THF is prepared, 6 mg of palladium(II) chloride (PdCl$_2$) is added thereto, and the mixture is stirred at the 0° C. for 55 minutes under a hydrogen gas atmosphere. Subsequently, 1.25 g of Merrifield resin (MR) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polyethyleneimine and Merrifield resin (PEI-Pd/MR) as a powder. Note that the polymer containing the plurality of first structural units and the plurality of second structural units correspond to polyethyleneimine (PEI) in this example, and an ethylene portion and a nitrogen atom bonding to the ethylene portion correspond to the plurality of first structural units and the plurality of second structural units, respectively.

[Chem. 3]

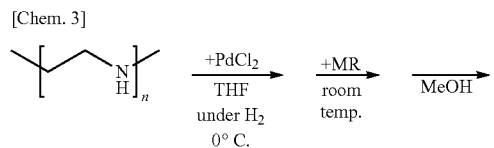

Example 4

A solution of 250 mg of poly(oxydimethylsilylene) in THF is prepared, 6 mg of palladium(II) chloride (PdCl$_2$) is added thereto, and the mixture is stirred at the 0° C. for 55 minutes under a hydrogen gas atmosphere. Subsequently, 1.25 g of hydrotalcite (HT) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and HT (PSiO—Pd/HT) as a powder.

[Chem. 4]

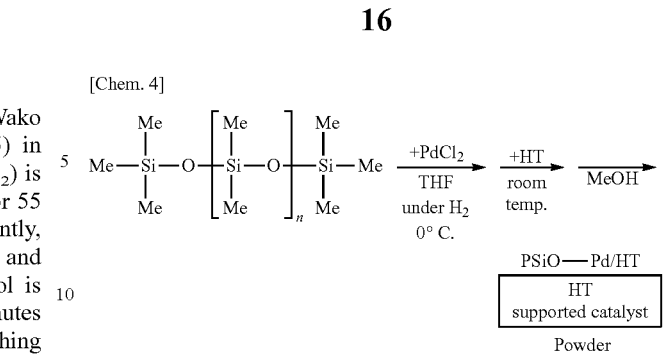

Example 5

A solution of 250 mg of polymethylene phenylene isocyanate (PMPP) (Sigma Aldrich, Catalog No. 406597) in THF is prepared, 6 mg of palladium(II) acetate is added thereto, and the mixture is stirred at the 0° C. for 55 minutes under a hydrogen gas atmosphere. Subsequently, 1.25 g of phenol resin (PR) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polymethylene phenylene isocyanate and phenol resin (PNCO—Pd/PR) as a powder.

[Chem. 5]

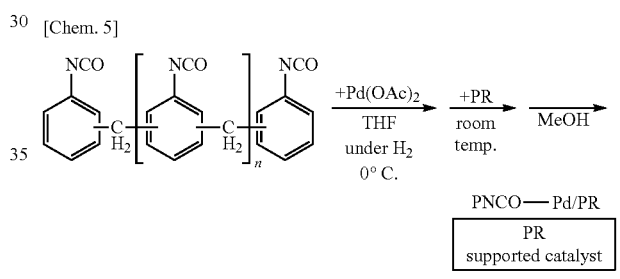

Example 6

A solution of 250 mg of poly(oxydimethylsilylene) (PDMS) in THF is prepared, 6 mg of palladium(II) acetate (Pd(OAc)$_2$) is added thereto, and the mixture is stirred at the 0° C. for 55 minutes under a hydrogen gas (H$_2$) atmosphere. Subsequently, 1.25 g of polystyrene (PS) is added to the mixture and stirred at room temperature for 25 minutes. Methanol (MeOH) is added thereto and the mixture is further stirred for 5 minutes to reprecipitate, followed by suction filtration and washing with methanol twice to obtain a palladium catalyst supported on poly(oxydimethylsilylene) and polystyrene (PSiO—Pd/PS) as a powder.

[Chem. 6]

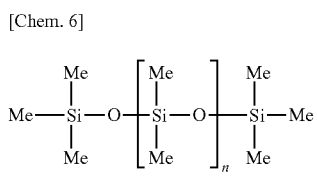 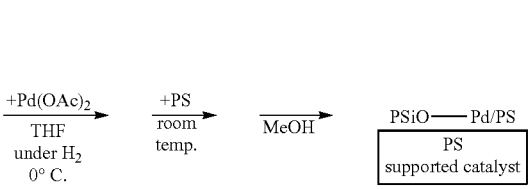

Example 7

A solution of 250 mg of poly(oxydimethylsilylene) in THF is prepared, 6 mg of palladium(II) nitrate (Pd(NO$_3$)$_2$) is added thereto, and the mixture is stirred at the 0° C. for 55 minutes under a hydrogen gas atmosphere. Subsequently, 1.25 g of silicon carbide (SiC) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and silicon carbide (PSiO—Pd/SiC) as a powder.

[Chem. 7]

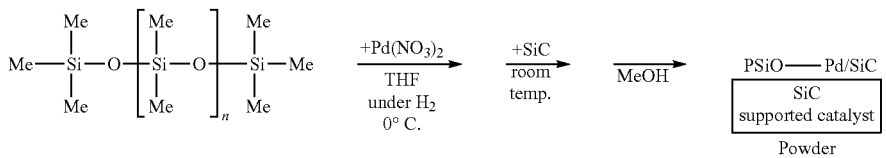

Example 8

A solution of 250 mg of polyethyleneimine (PEI) in THF is prepared, 6 mg of palladium(II) chloride (PdCl$_2$) is added thereto, and the mixture is stirred at the 0° C. for 55 minutes under a hydrogen gas atmosphere. Subsequently, 1.25 g of niobium oxide (Nb$_2$O$_5$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polyethyleneimine and niobium oxide (PEI-Pd/Nb$_2$O$_5$) as a powder.

[Chem. 8]

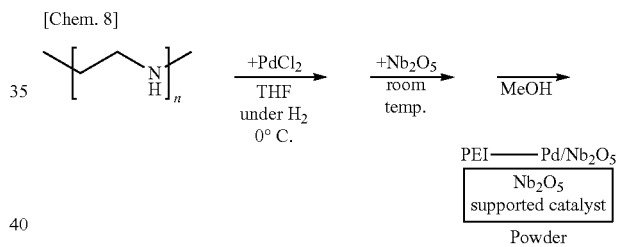

Example 9

A solution of 250 mg of poly(oxydimethylsilylene) in THF is prepared, 6 mg of palladium(II) chloride is added thereto, and the mixture is stirred at the 0° C. for 55 minutes under a hydrogen gas atmosphere. Subsequently, 1.25 g of tantalum oxide (Ta$_2$O$_5$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and tantalum oxide (PSiO—Pd/Ta$_2$O$_5$) as a powder.

[Chem. 9]

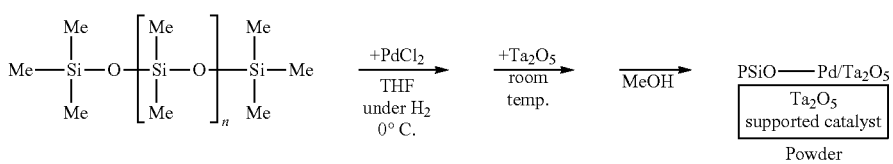

Example 10

A solution of 250 mg of polymethylene phenylene isocyanate (PMPP) in THF is prepared, 6 mg of palladium(II) acetate is added thereto, and the mixture is stirred at the 0° C. for 55 minutes under a hydrogen gas atmosphere. Subsequently, 1.25 g of ytterbium oxide ($Yb_2O_3$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polymethylene phenylene isocyanate and ytterbium oxide (PNCO—Pd/$Yb_2O_3$) as a powder.

[Chem. 10]

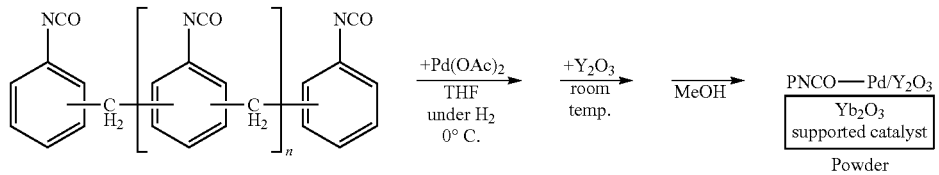

Example 11

A suspension of 250 mg of poly(oxydimethylsilylene) and 5 mg of sodium borohydride ($NaBH_4$) in THF is prepared, 6 mg of palladium(II) acetate is added thereto, and the mixture is stirred at the 0° C. for 55 minutes. Subsequently, 1.25 g of complex oxide of magnesium and lanthanum (MgLaO) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and complex oxide of magnesium and lanthanum (PSiO—Pd/MgLaO) as a powder.

[Chem. 11]

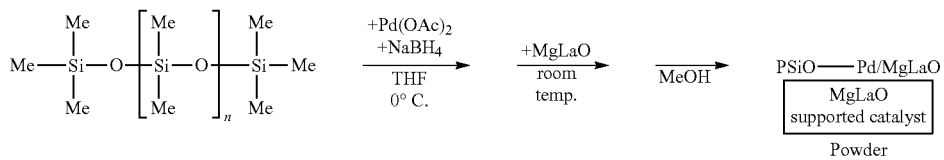

Example 12

A suspension of 250 mg of poly(oxydimethylsilylene) and 5 mg of sodium borohydride in THF is prepared, 6 mg of palladium(II) nitrate is added thereto, and the mixture is stirred at the 0° C. for 55 minutes. Subsequently, 1.25 g of cerium oxide ($CeO_2$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and cerium oxide (PSiO—Pd/$CeO_2$) as a powder.

[Chem. 12]

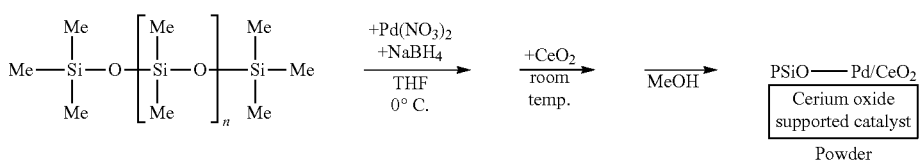

Example 13

A suspension of 250 mg of polyethyleneimine and 5 mg of sodium borohydride in THF is prepared, 6 mg of palladium(II) chloride is added thereto, and the mixture is stirred at the 0° C. for 55 minutes. Subsequently, 1.25 g of Merrifield resin (MR) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polyethyleneimine and Merrifield resin (PEI-Pd/MR) as a powder.

[Chem. 13]

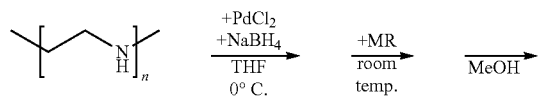

[Chem. 14]

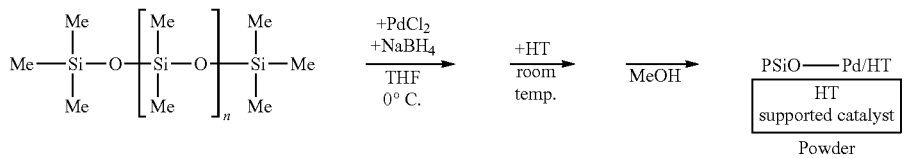

Example 14

A suspension of 250 mg of poly(oxydimethylsilylene) and 5 mg of sodium borohydride in THF is prepared, 6 mg of palladium(II) chloride is added thereto, and the mixture is stirred at the 0° C. for 55 minutes. Subsequently, 1.25 g of hydrotalcite (HT) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and hydrotalcite (PSiO—Pd/HT) as a powder.

Example 15

A suspension of 250 mg of polymethylene phenylene isocyanate and 5 mg of sodium borohydride in THF is prepared, 6 mg of palladium(II) acetate is added thereto, and the mixture is stirred at the 0° C. for 55 minutes. Subsequently, 1.25 g of phenol resin (PR) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polymethylene phenylene isocyanate and phenol resin (PNCO—Pd/PR) as a powder.

[Chem. 15]

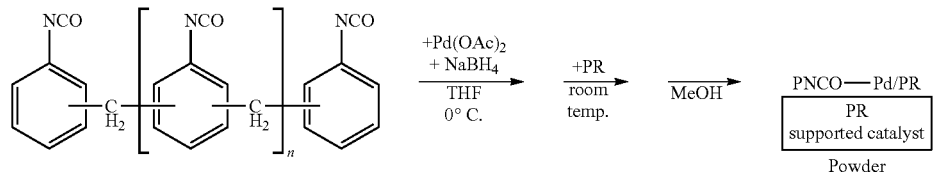

Example 16

A suspension of 250 mg of poly(oxydimethylsilylene) and 5 mg of sodium borohydride (NaBH$_4$) in THF is prepared, 6 mg of palladium(II) acetate is added thereto, and the mixture is stirred at the 0° C. for 55 minutes. Subsequently, 1.25 g of polystyrene (PS) is added to the mixture and stirred at room temperature for 25 minutes. Methanol (MeOH) is added thereto and the mixture is further stirred for 5 minutes to reprecipitate, followed by suction filtration and washing with methanol twice to obtain a palladium catalyst supported on poly(oxydimethylsilylene) and polystyrene (PSiO—Pd/PS) as a powder.

[Chem. 16]

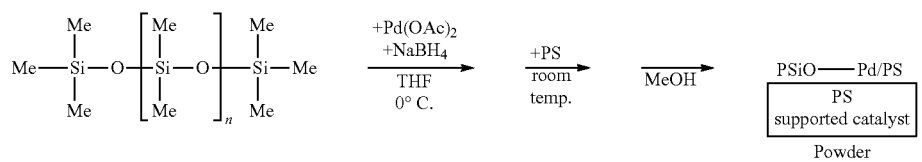

Example 17

A suspension of 250 mg of poly(oxydimethylsilylene) and 5 mg of sodium borohydride in THF is prepared, 6 mg of palladium(II) nitrate is added thereto, and the mixture is stirred at the 0° C. for 55 minutes. Subsequently, 1.25 g of silicon carbide (SiC) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and silicon carbide (PSiO—Pd/SiC) as a powder.

[Chem. 17]

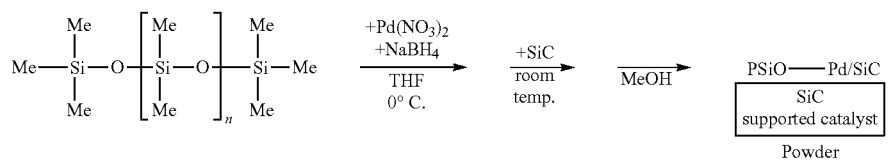

Example 18

A suspension of 250 mg of polyethyleneimine and 5 mg of sodium borohydride in THF is prepared, 6 mg of palladium(II) chloride is added thereto, and the mixture is stirred at the 0° C. for 55 minutes. Subsequently, 1.25 g of niobium oxide ($Nb_2O_5$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polyethyleneimine and niobium oxide (PEI-Pd/$Nb_2O_5$) as a powder.

[Chem. 18]

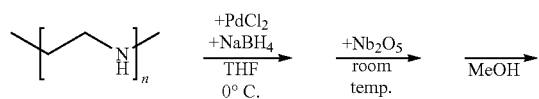

-continued

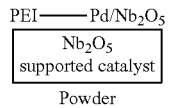

Example 19

A suspension of 250 mg of poly(oxydimethylsilylene) (PDMS) and 5 mg of sodium borohydride in THF is prepared, 6 mg of palladium(II) chloride is added thereto, and the mixture is stirred at the 0° C. for 55 minutes. Subsequently, 1.25 g of tantalum oxide ($Ta_2O_5$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on poly(oxydimethylsilylene) and tantalum oxide (PSiO—Pd/$Ta_2O_5$) as a powder.

Example 20

A suspension of 250 mg of polymethylene phenylene isocyanate and 5 mg of sodium borohydride in THF is prepared, 6 mg of palladium(II) acetate is added thereto, and the mixture is stirred at the 0° C. for 55 minutes. Subsequently, 1.25 g of ytterbium oxide ($Yb_2O_3$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on polymethylene phenylene isocyanate and ytterbium oxide (PNCO—Pd/$Yb_2O_3$) as a powder.

[Chem. 19]

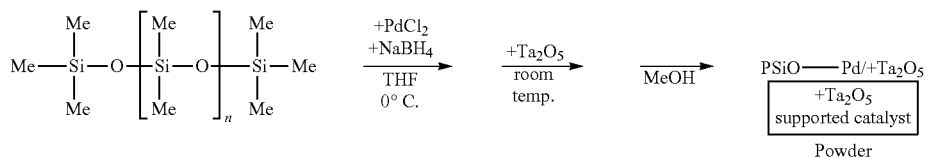

[Chem. 20]

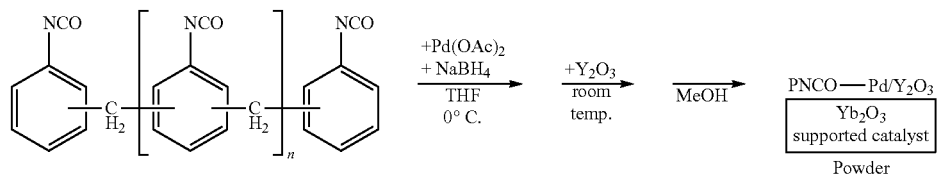

Example 21

A solution of 250 mg of poly(oxydimethylsilylene)(oxymethylhydrosilylene) (PMHS) (Shin-Etsu Silicone, Catalog No. KF-99) in THF is prepared, 6 mg of palladium (II) acetate is added thereto, and the mixture is stirred at the 0° C. for 55 minutes. At this time, the palladium(II) acetate is reduced by the reducing ability derived from the silicon-hydrogen bond of poly(oxydimethylsilylene)(oxymethylhydrosilylene) to generate a zero valent palladium cluster. Subsequently, 1.25 g of complex oxide of magnesium and lanthanum (MgLaO) is added to the mixture and stirred at room temperature for 25 minutes. Methanol (MeOH) is added thereto and the mixture is further stirred for 5 minutes to reprecipitate, followed by suction filtration and washing with methanol twice to obtain a palladium catalyst supported on MgLaO (PSiOH—Pd/MgLaO) as a powder. Note that the polymer containing the plurality of first structural units and the plurality of second structural units corresponds to poly(oxydimethylsilylene)(oxymethylhydrosilylene) in this example, and for example, it is interpreted that a methylhydrosilylene portion and an oxygen atom bonding to the methylhydrosilylene portion correspond to the plurality of first structural units and the plurality of second structural units, respectively.

[Chem. 21]

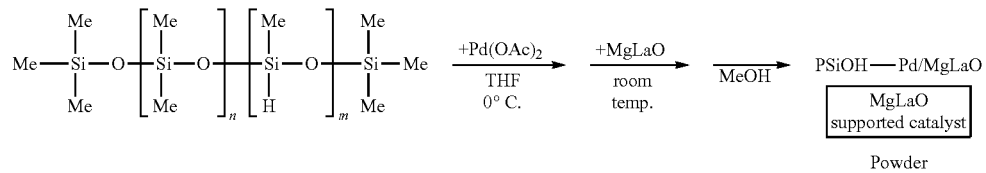

Example 22

A solution of 250 mg of poly(oxydimethylsilylene)(oxymethylhydrosilylene) in THF is prepared, 6 mg of palladium(II) nitrate is added thereto, and the mixture is stirred at the 0° C. for 55 minutes. Subsequently, 1.25 g of cerium oxide ($CeO_2$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on cerium oxide (PSiOH—Pd/$CeO_2$) as a powder.

[Chem. 22]

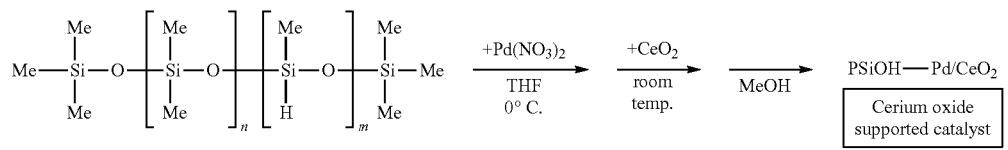

Example 23

A solution of 250 mg of poly(oxydimethylsilylene)(oxymethylhydrosilylene) in THF is prepared, 6 mg of palladium(II) chloride is added thereto, and the mixture is stirred at the 0° C. for 55 minutes. Subsequently, 1.25 g of Merrifield resin (MR) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on Merrifield resin (PSiOH—Pd/MR) as a powder.

[Chem. 23]

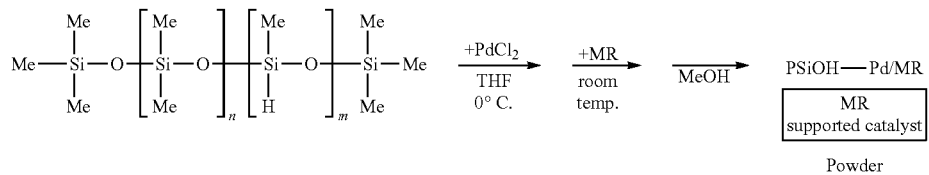

Example 24

A solution of 250 mg of poly(oxydimethylsilylene)(oxymethylhydrosilylene) in THF is prepared, 6 mg of palladium(II) chloride is added thereto, and the mixture is stirred at the 0° C. for 55 minutes. Subsequently, 1.25 g of hydrotalcite (HT) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on hydrotalcite (PSiOH—Pd/HT) as a powder.

[Chem. 24]

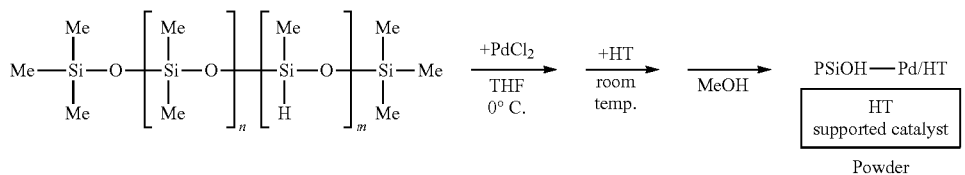

Example 25

A solution of 250 mg of poly(oxydimethylsilylene)(oxymethylhydrosilylene) in THF is prepared, 6 mg of palladium(II) acetate is added thereto, and the mixture is stirred at the 0° C. for 55 minutes. Subsequently, 1.25 g of phenol resin (PR) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on phenol resin (PSiOH—Pd/PR) as a powder.

[Chem. 25]

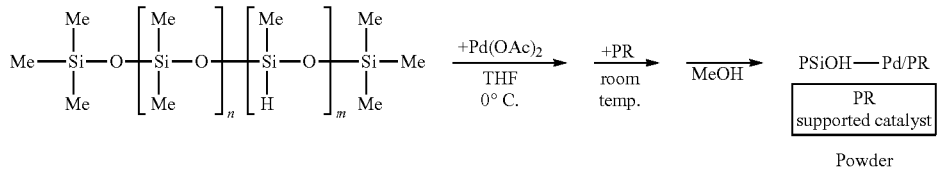

Example 26

A solution of 250 mg of poly(oxydimethylsilylene)(oxymethylhydrosilylene) in THF is prepared, 6 mg of palladium(II) acetate is added thereto, and the mixture is stirred at the 0° C. for 55 minutes. Subsequently, 1.25 g of polystyrene (PS) is added to the mixture and stirred at room temperature for 25 minutes. Methanol (MeOH) is added thereto and the mixture is further stirred for 5 minutes to reprecipitate, followed by suction filtration and washing with methanol twice to obtain a palladium catalyst supported on polystyrene (PSiOH—Pd/PS) as a powder.

[Chem. 26]

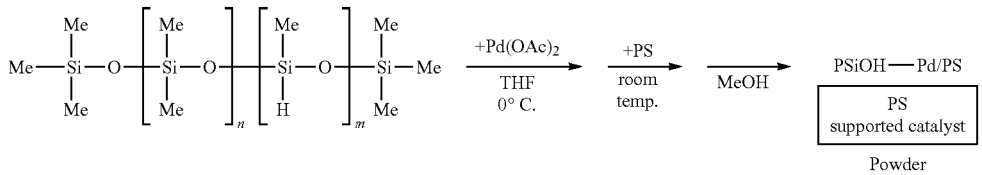

Example 27

A solution of 250 mg of poly(oxydimethylsilylene)(oxymethylhydrosilylene) in THF is prepared, 6 mg of palladium(II) nitrate is added thereto, and the mixture is stirred at the 0° C. for 55 minutes. Subsequently, 1.25 g of silicon carbide (SiC) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on silicon carbide (PSiOH—Pd/SiC) as a powder.

[Chem. 27]

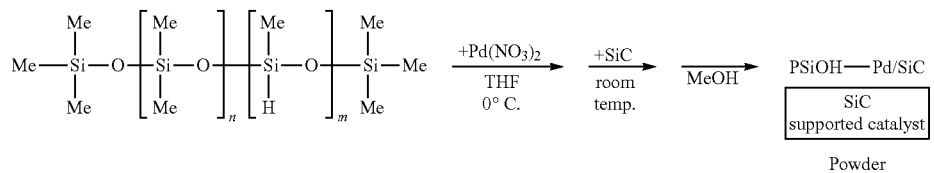

Example 28

A solution of 250 mg of poly(oxydimethylsilylene)(oxymethylhydrosilylene) in THF is prepared, 6 mg of palladium(II) chloride is added thereto, and the mixture is stirred at the 0° C. for 55 minutes. Subsequently, 1.25 g of niobium oxide ($Nb_2O_5$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on niobium oxide (PSiOH—Pd/$Nb_2O_5$) as a powder.

[Chem. 28]

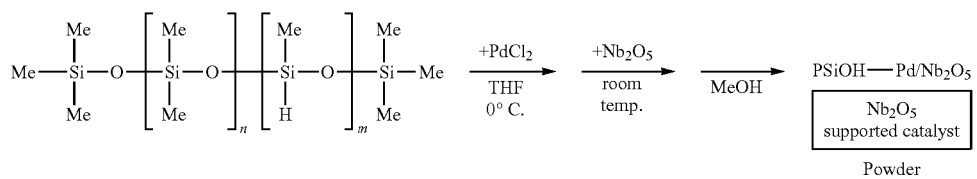

Example 29

A solution of 250 mg of poly(oxydimethylsilylene)(oxymethylhydrosilylene) in THF is prepared, 6 mg of palladium(II) chloride is added thereto, and the mixture is stirred at the 0° C. for 55 minutes. Subsequently, 1.25 g of tantalum oxide ($Ta_2O_5$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on tantalum oxide (PSiOH—Pd/$Ta_2O_5$) as a powder.

[Chem. 29]

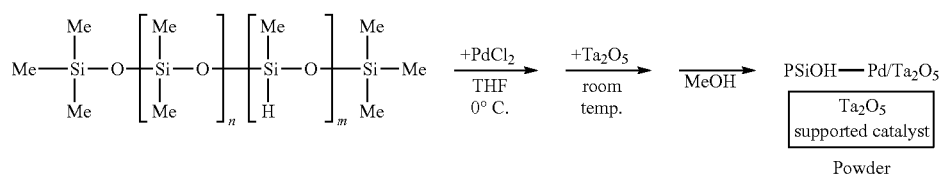

Example 30

A solution of 250 mg of poly(oxydimethylsilylene)(oxymethylhydrosilylene) in THF is prepared, 6 mg of palladium(II) acetate is added thereto, and the mixture is stirred at the 0° C. for 55 minutes. Subsequently, 1.25 g of ytterbium oxide ($Yb_2O_3$) is added to the mixture and stirred at room temperature for 25 minutes. Methanol is added thereto and the mixture is further stirred for 5 minutes to reprecipitate, followed by suction filtration and washing with methanol twice to obtain a palladium catalyst supported on ytterbium oxide (PSiOH—Pd/$Yb_2O_3$) as a powder.

[Chem. 30]

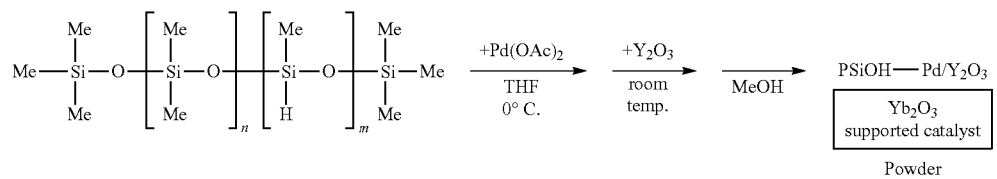

Example 31

Complex oxide of magnesium and lanthanum (MgLaO) is added to a 50 ml of ethanol solution of 4.4 mg of sodium tetrachloropalladate(II) to prepare a dispersion, and the dispersion is stirred for 12 hours. Next, a THF solution containing 250 mg of poly(oxydimethylsilylene)(oxymethylhydrosilylene) is added to the dispersion, and the mixture is stirred at room temperature for 3 hours. Methanol is added thereto and the mixture is further stirred for 5 minutes to reprecipitate, followed by suction filtration and washing with methanol twice to obtain a palladium catalyst supported on complex oxide of magnesium and lanthanum (PSiOH—Pd/MgLaO*) as a powder. Note that when a metal atom is supported on a substrate containing an ion having a highly positive charge density such as a lanthanoid having a valence of 3 or more as in the present example, the loading ratio tends to be improved due to the Coulomb interaction by contacting an ion containing the metal atom.

Example 32

Complex oxide of magnesium and lanthanum (MgLaO) is added to a 50 ml of ethanol solution of 4.4 mg of sodium tetrachloropalladate(II) to prepare a dispersion and the dispersion is stirred for 12 hours. Next, an ethanol solution containing 50 mg of hydrazine monohydrate is added to the dispersion, and the mixture is stirred at room temperature for 3 hours. Methanol is added thereto and the mixture is further stirred for 5 minutes to reprecipitate, followed by suction filtration and washing with methanol twice to obtain a palladium catalyst supported on complex oxide of magnesium and lanthanum (PSiOH—Pd/MgLaO**) as a powder. Note that when a metal atom is supported on a substrate containing an ion having a highly positive charge density such as a lanthanoid having a valence of 3 or more as in the present example, the loading ratio tends to be improved due to the Coulomb interaction by contacting an ion containing the metal atom.

<Manufacturing of Compound Using Supported Metal Catalyst>

When several metal catalysts synthesized by the above method are used, the catalysts have high catalytic activity in various chemical reactions. In addition, after completion of the reactions, the catalysts are recovered by separating into a solid and a filtrate. When a metal concentration of the filtrate is examined by EDX or the like, leakage hardly occurs in any of the catalysts, and the polymer has high holding ability. In some catalysts, leakage of metal is not confirmed at all by the used detection method, and a highly durable catalyst can be obtained.

[Reduction Reaction Using Supported Metal Catalyst]

A hexane solution of 1.0 mmol of a reaction substrate is prepared, 10 mg of a palladium catalyst is added thereto to prepare a suspension, and the suspension is stirred at room temperature for several hours under a hydrogen gas atmosphere of 1 atm. Thereafter, the palladium catalyst is removed from the suspension by filtration. Subsequently, the filtrate is concentrated and purified by column chromatography to obtain the corresponding reduced compound.

In a hydrogenation reaction of a compound having three or more substituents on a double bond as described below, usual metal catalysts require heating. However, it is remarkable that the metal catalyst supported on a metal atom of at least one of an alkaline earth metal and a lanthanoid (preferably both of an alkaline earth metal and a lanthanoid), such as the palladium catalyst supported on MgLaO (PSiO—Pd/MgLaO) described in Example 1 and the palladium catalyst supported on MgLaO (PSiOH—Pd/MgLaO) described in Example have a high catalytic activity.

[Chem. 31]

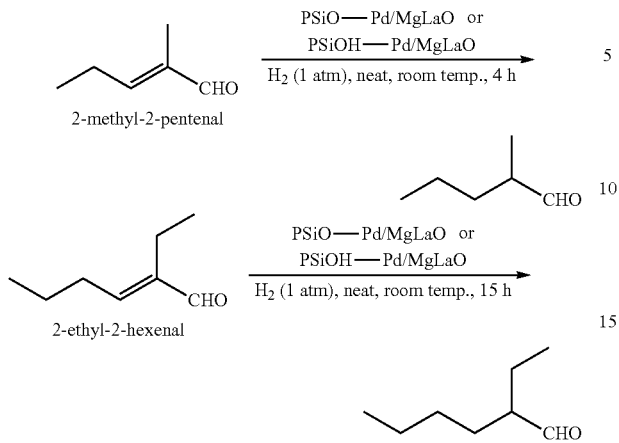

[Tuji-Trost Reaction Using Supported Metal Catalyst]

A solution of 2 mmol of diallyl carbonate (K) and 1 mmol of β-keto ester (L) in dehydrated tetrahydrofuran (THF) is added dropwise to a suspension of 0.05 mmol of one of some palladium catalysts of Examples 1 to 30 and 0.1 mmol of PPh$_3$ in dehydrated THF, and the mixture is stirred for several hours. Thereafter, the palladium catalyst is removed from the suspension by filtration. The filtrate is then concentrated and purified by column chromatography to obtain an allylated product (M).

[Chem. 32]

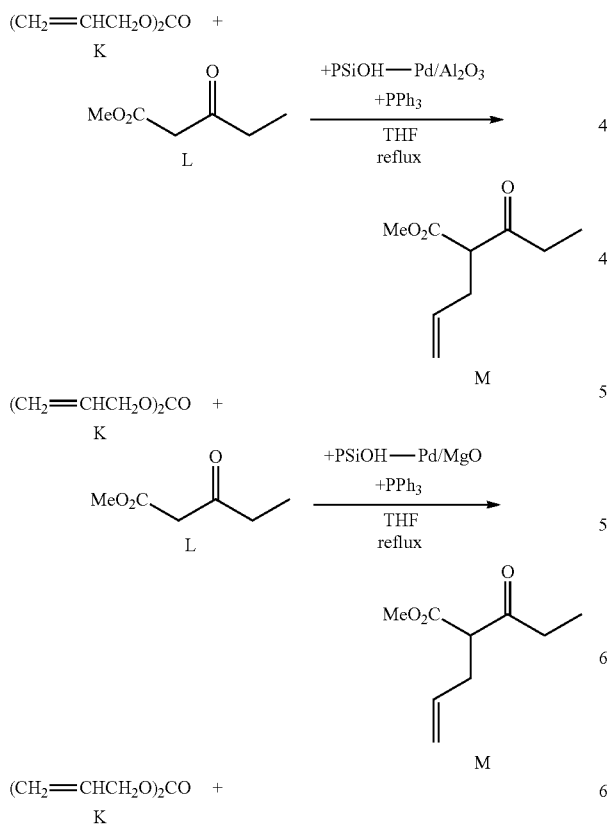

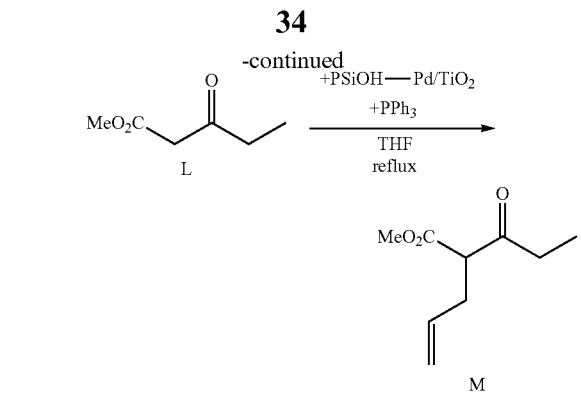

[Fukuyama Coupling Using Supported Metal Catalyst]

A solution of 1.5 mmol of ethylzinc iodide (EtZnI) in dehydrated THF is added dropwise to a suspension of 0.05 mmol of one of some palladium catalysts of Examples 1 to 30 and 1.0 mmol of thioester (N) in dehydrated toluene, and the mixture is stirred for several hours. Thereafter, the palladium catalyst is removed from the suspension by filtration. Subsequently, the filtrate is concentrated and purified by column chromatography to obtain a ketone (O) which is a coupling product.

[Chem. 33]

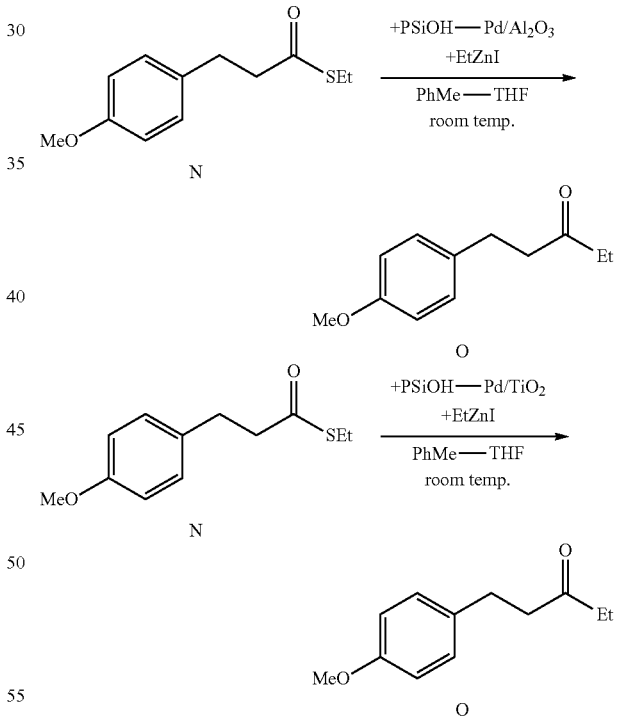

[Stille Coupling Using Supported Metal Catalyst]

A solution of 1 mmol of benzoyl chloride (P) in HMPA is added dropwise to a suspension of 0.05 mmol of one of some palladium catalysts of Examples 1 to 30 and 1 mmol of tetraphenyltin (Q) in HMPA, and the mixture is stirred at 65° C. for several hours. Thereafter, the palladium catalyst is removed from the suspension by filtration. Subsequently, the filtrate is concentrated and purified by column chromatography to obtain benzophenone (R) which is a coupling product.

[Chem. 34]

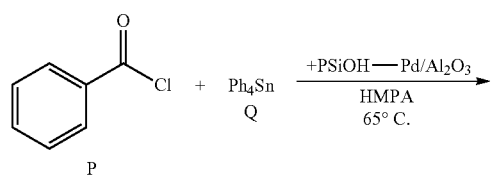

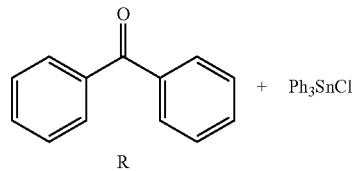

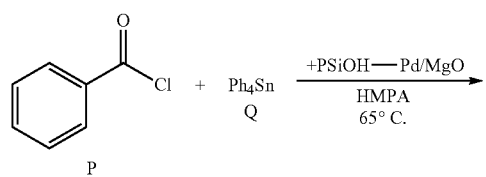

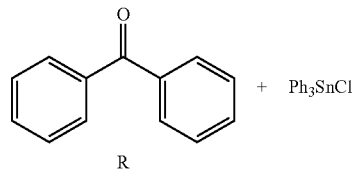

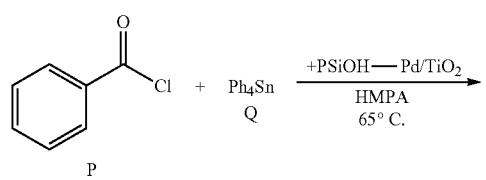

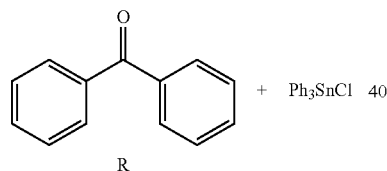

[Catellani Reaction Using Supported Metal Catalyst]

A solution of 1 mmol of o-iodotoluene (S), 2 mmol of aminoethyl bromide (T) and 2.0 mmol of methyl acrylate (U) in DMF is added dropwise to a suspension of 0.1 mmol of one of some palladium catalysts of Examples 1 to 30, 0.2 mmol of tri(2-furyl)phosphine (TFP), 2.0 mmol of norbornene and $Ce_2CO_3$ in DMF, and the mixture is stirred at 100° C. for several hours. Thereafter, the palladium catalyst is removed from the suspension by filtration. Subsequently, the filtrate is concentrated and purified by column chromatography to obtain a coupling product (V).

[Chem. 35]

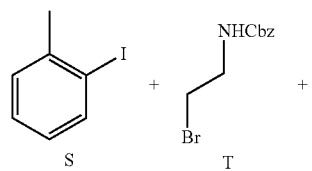

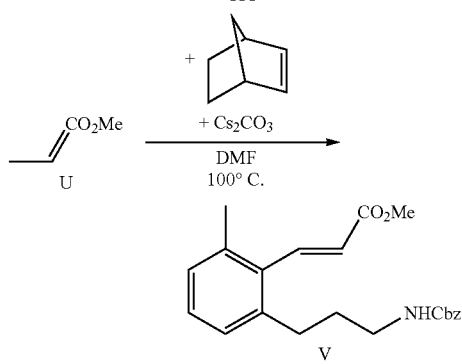

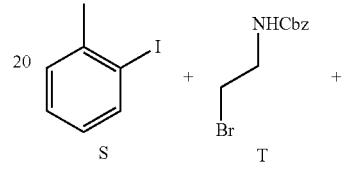

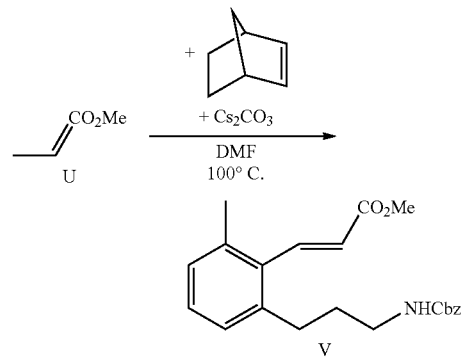

[Negishi Coupling Using Supported Metal Catalyst]

A solution of 1 mmol of 4-iodoanisole (W) and 1 mmol of phenylzinc chloride in THF is added dropwise to a suspension of 0.05 mmol of one of some palladium catalysts of Examples 1 to 30 in dehydrated THF, and the mixture is stirred for several hours. Thereafter, the palladium catalyst is removed from the suspension by filtration. Subsequently, the filtrate is concentrated and purified by column chromatography to obtain methoxybiphenyl (X) which is a coupling product.

[Chem. 36]

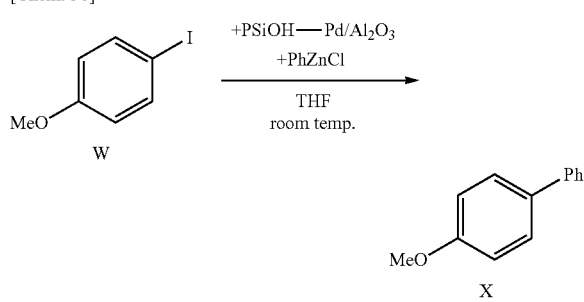

-continued

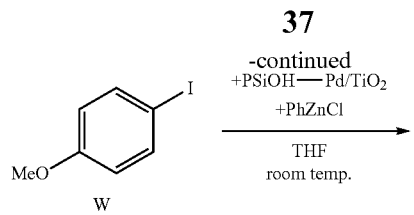

palladium catalyst is removed from the suspension by filtration. Subsequently, the filtrate is concentrated and purified by column chromatography to obtain tertiary amine (D') which is a coupling product.

[Chem. 38]

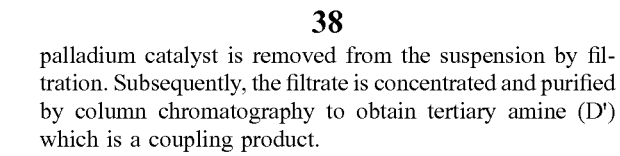

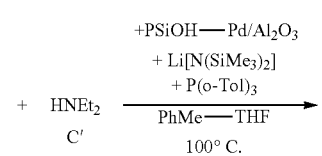

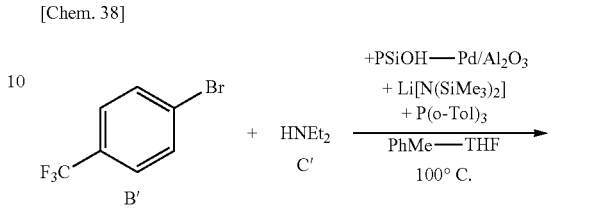

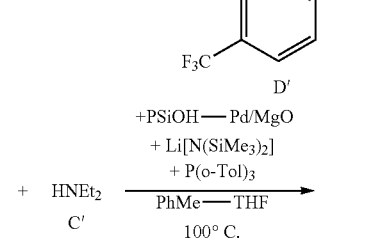

[Larock Indole Synthesis Using Supported Metal Catalyst]

A solution of 1 mmol of 2-iodoaniline (Y), 3 mmol of 4-octyne (Z) and 0.1 mmol of $PPh_3$ in DMF is added dropwise to a suspension of 0.05 mmol of one of some palladium catalysts of Examples 1 to 30, 1 mmol of n-$Bu_4NCl$ and 5 mmol of $K_2CO_3$ in DMF, and the mixture is stirred at 100° C. for several hours. Thereafter, the palladium catalyst is removed from the suspension by filtration. Subsequently, the filtrate is concentrated and purified by column chromatography to obtain a substituted indole (A').

[Chem. 37]

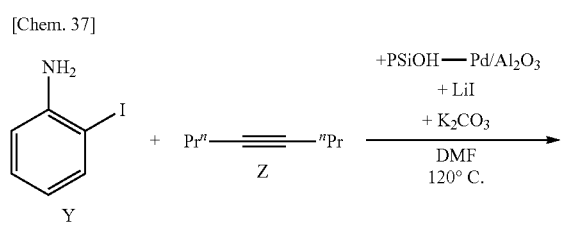

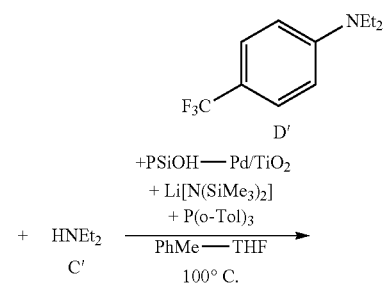

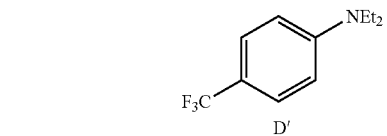

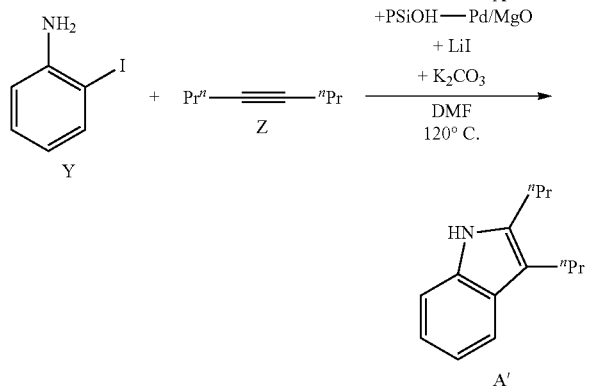

[Kumada Coupling Using Supported Metal Catalyst]

A solution of 1.2 mmol of 4-(methoxycarbonyl)phenylmagnesium chloride (E') in dehydrated THF is added dropwise at −40° C. to a suspension of 0.05 mmol of one of some palladium catalysts of Examples 1 to 30, 0.05 mmol of 1,1'-bis(diphenylphosphinophosphine) (dppf) and 1.0 mmol of 2-chloropyrimidine (F') in dehydrated THF, and the mixture is stirred at room temperature for several hours. Thereafter, the palladium catalyst is removed from the suspension by filtration. Subsequently, the filtrate is concentrated and purified by column chromatography to obtain a substituted biaryl (G') which is a coupling product.

[Hartwig Reaction Using Supported Metal Catalyst]

A solution of 1.2 mmol of lithium hexamethyldisilazide (LiN($SiMe_3$)$_2$) in dehydrated THF is added dropwise to a suspension of 0.05 mmol of one of some palladium catalysts of Examples 1 to 30, 0.10 mmol of tri(o-tolyl)phosphine, 1.0 mmol of 1-bromo-4-trifluoromethylbenzene (B') and 1.5 mmol of diethylamine (C') in dehydrated toluene, and the mixture is stirred at 100° C. for several hours. Thereafter, the

[Chem. 39]

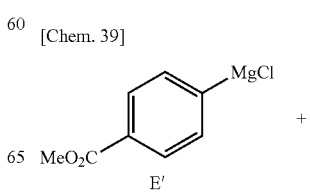

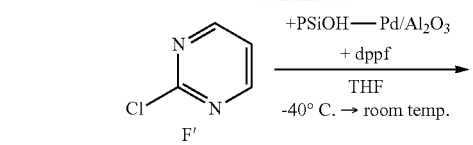

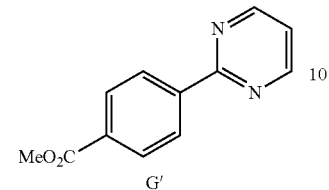

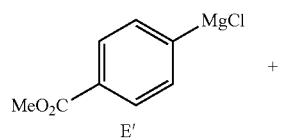

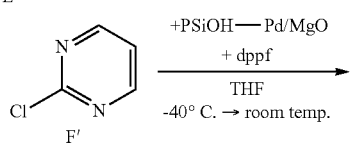

[Hiyama Coupling Using Supported Metal Catalyst]

A solution of 1.2 mmol of tris(dimethylamino)sulfonium difluorotrimethylsilicate (TASF) in HMPA is added dropwise to a suspension of 0.05 mmol of one of some palladium catalysts of Examples 1 to 30, 1.2 mmol of trimethylvinylsilane (I') and 1 mmol of p-iodotoluene (H') in HMPA, and the mixture is stirred at 50° C. for several hours. Thereafter, the palladium catalyst is removed from the suspension by filtration. Subsequently, the filtrate is concentrated and purified by column chromatography to obtain 4-methylstyrene (J') which is a coupling product.

[Chem. 40]

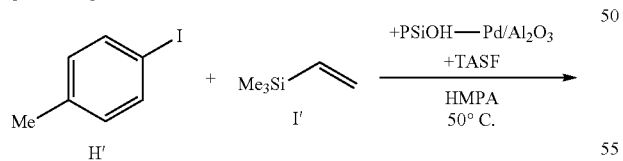

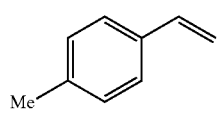

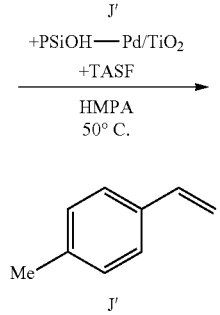

[Marshall Propargylation Reaction Using Supported Metal Catalyst]

A solution of 1.0 mmol of isobutyraldehyde (K') in THF is added dropwise to a suspension of 0.05 mmol of one of some palladium catalysts of Examples 1 to 30, 0.10 mmol of PPh$_3$, 1.5 mmol of InI and 1.3 mmol of alkyne (L') in HMPA, and the mixture is stirred at 0° C. for several hours. Thereafter, the palladium catalyst is removed from the suspension by filtration. Subsequently, the filtrate is concentrated and purified by column chromatography to obtain a homopropargyl alcohol (M') which is a coupling product.

[Chem. 41]

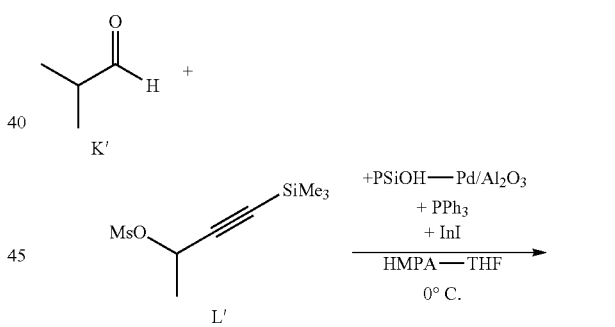

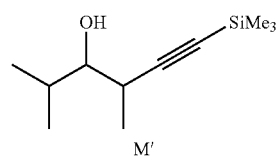

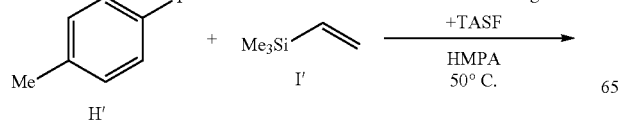

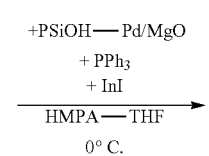

-continued

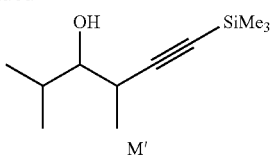

M'

[Cyanation Reaction Using Supported Metal Catalyst]

A solution of 1.0 mmol of bromobenzene (O') in NMP is added dropwise to a suspension of 0.05 mmol of one of some palladium catalysts of Examples 1 to 30, 0.10 mmol of 1,1'-bis(diphenylphosphinophosphine) (dppf), 1.0 mmol of sodium carbonate and 0.25 mmol of potassium ferrocyanide in NMP, and the mixture is stirred at 140° C. for several hours. Thereafter, the palladium catalyst is removed from the suspension by filtration. Subsequently, the filtrate is concentrated and purified by column chromatography to obtain benzonitrile (O') which is a coupling product.

[Chem. 42]

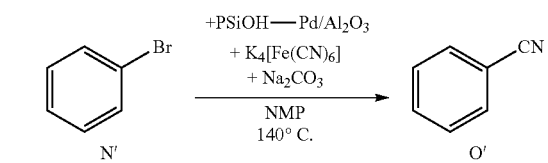

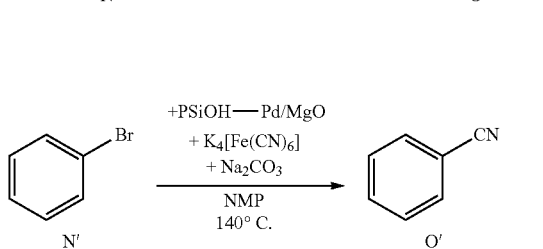

[Aminocarbonylation Reaction Using Supported Metal Catalyst]

A suspension of 0.05 mmol of one of some palladium catalysts of Examples 1 to 30, 0.15 mmol of 1,1'-bis(diphenylphosphinophosphine) (dppf), 1.5 mmol of triethylamine, 1.0 mmol of 5-bromoindole (P') and 1.5 mmol of piperidine (Q') in toluene is stirred in autoclave for several hours under the conditions 25 atm, 130° C., and CO gas atmosphere. Thereafter, the palladium catalyst is removed from the suspension by filtration. Subsequently, the filtrate is concentrated and purified by column chromatography to obtain a substituted indole (R') which is an aminocarbonylated product.

[Chem. 43]

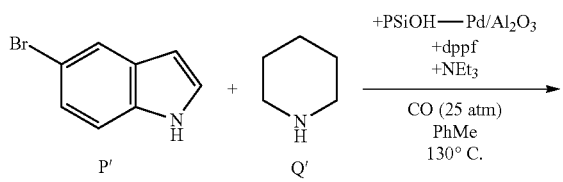

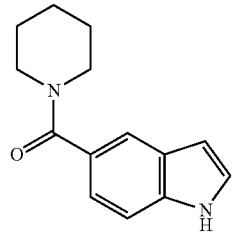

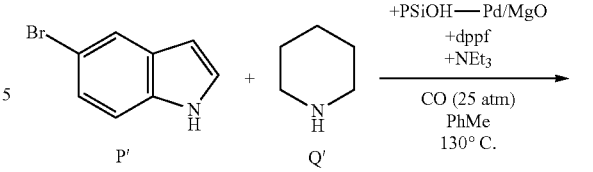

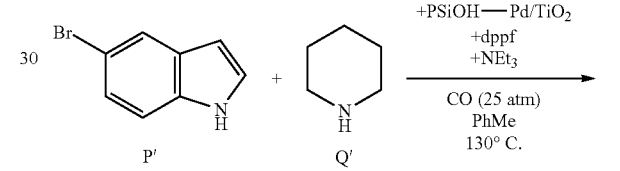

Note that FIG. 1 describes a schematic diagram of an apparatus in a flow reactor. A reaction substrate A and a reaction substrate B are each delivered in the direction of 4 (column filled with catalyst) by 1 (flow control unit or pump) and 2 (flow control unit or pump). At this time, it is preferred to join the reaction substrate A and the reaction substrate B at a junction 3. As a result, localization of the reaction substrate A and the reaction substrate B in 4 (column filled with the catalyst) is suppressed, and encounter probability between a molecule of the reaction substrate A and a molecule of the reaction substrate B is improved. A temperature of 4 (column filled with catalyst) is controlled by 5 (temperature controller).

The supported catalyst of Examples 1 to 32 and the catalyst of the present invention can be applied to the flow reactor described above and the above reaction examples can also be carried out by the flow reactor. When filling the catalyst in the column, in addition to the catalyst, a compound such as silicon oxide ($SiO_2$) and an oxide containing titanium, zirconium, magnesium and aluminum can be used appropriately as a balancer, and more specifically, titanium oxide (TiO$_2$), zirconium oxide (ZrO$_2$), magnesium oxide (MgO), alumina (Al$_2$O$_3$), zeolite, hydrotalcite and the like can be used. A ceramic such as silicon carbide, silicon nitride and boron nitride, and a carbon material such as diamond and carbon fiber can also be used. Adding the balancer as described above may have the effect of improving a reaction yield and increasing a number of times of repeated use of the catalyst even in a batch reaction. In addition, in the flow reaction, when the reaction substrate passes through the column of the flow reactor, the addition may contribute to stabilization of pressure and flow rate or limitation of pressure loss.

Reaction examples using the flow reactor described in FIG. 1 and the above-described supported catalyst are described below. When applied to the hydrogenation reaction of 2-methylpentenal, squalene or the like which are compounds having three or more substituents on the double bond as described above, also even in the flow reaction, the double bond is quickly and quantitatively reduced to obtain 2-methylpentanal and squalane, respectively. Note that a catalyst obtained by adding alumina as a balancer to the supported catalyst manufactured in the above Example 32 is used.

[Chem. 44]

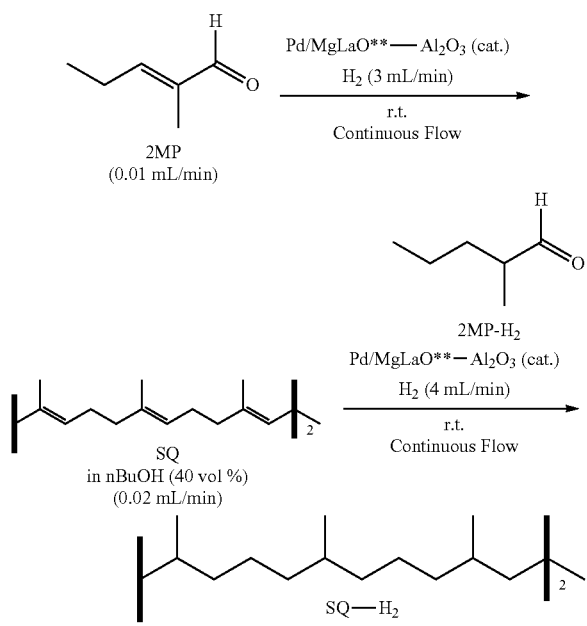

By using the flow reactor as described above, it is possible to use the catalyst repeatedly without going through a step of reusing the catalyst by filtration or the like after the reaction. Since the catalyst according to the present invention can reduce the leakage and deterioration of the metal even when an expensive metal is used as the catalytic center, the frequency of refilling the flow column can be reduced. It is advantageous to apply the catalyst according to the present invention to a flow reactor.

The invention claimed is:
1. A catalyst comprising:
   a substrate; and
   a first metal atom as a catalytic center supported on the substrate,
   wherein the substrate contains a non-metallic atom and a second metal atom,
   the non-metallic atom being any one selected from the group consisting of a group 15 element, a group 16 element and a group 17 element, and
   the second metal being a lanthanoid.

2. The catalyst of claim 1, further comprising a polymer containing a plurality of first structural units and a plurality of second structural units,
   wherein at least a part of the first metal atom and the substrate is covered with the polymer.

3. The catalyst of claim 2, wherein:
   at least one first structural unit of the plurality of first structural units of the polymer has a first constituent atom constituting at least a part of a main chain of the polymer and a first substituent bonding to the first constituent atom; and
   a second substituent atom contained in each of the plurality of second structural units of the polymer bonds to the first constituent atom,
      where the second constituent atom is different from the first constituent atom, or at least one substituent among all substituents on the second constituent atom is different from the first substituent.

4. The catalyst of claim 3, wherein the main chain of the polymer does not contain a carbon atom.

5. The catalyst of claim 3, wherein neither the first constituent atom nor the second constituent atom is a carbon atom.

6. The catalyst of claim 3, wherein the first constituent atom is a silicon atom.

7. The catalyst of claim 3, wherein the second constituent atom is an oxygen atom or a nitrogen atom.

8. The catalyst of claim 1, wherein the first metal atom is any one selected from the group consisting of palladium, platinum, ruthenium, rhodium, silver, gold, copper, nickel, cobalt, iron, chromium, manganese, scandium, indium, lanthanoid, technetium, osmium, molybdenum, tungsten, iridium, rhenium, titanium, zirconium, hafnium, tantalum, niobium and vanadium.

9. The catalyst of claim 3, wherein:
   the first constituent atom is a silicon atom; and
   the first substituent is at least one of a substituent consisting only of a hydrogen atom, a substituent containing an oxygen atom and a substituent containing a carbon atom.

10. A method for manufacturing a catalyst comprising:
    preparing a first substance containing a first metal atom;
    preparing a substrate for supporting the first metal atom, the substrate containing a non-metallic atom and a second metal atom, the non-metallic atom being selected from the group consisting of a group 15 element, a group 16 element and a group 17 element, and the second metal atom being a lanthanoid; and
    contacting the first substance and the substrate to obtain the catalyst.

11. The method of claim 10, further comprising:
    preparing a polymer containing a plurality of first structural units and a plurality of second structural units; and
    reacting the first substance and the polymer.

12. The method of claim 11, wherein:
    at least one first structural unit of the plurality of first structural units has a first constituent atom constituting at least a part of a main chain of the polymer and a first substituent bonding to the first constituent atom; and a second constituent atom contained in each of the plurality of second structural units bonds to the first constituent atom, where the second constituent atom is different from the first constituent atom, or at least one substituent among all substituents on the second constituent atom is different from the first substituent.

13. The method of claim 12, wherein in reacting the first substance and the polymer, a reaction of the first substituent and the first substance occurs.

14. The method of claim 12, wherein:
the first constituent atom is a silicon atom; and
the first substituent is a hydrogen atom.

15. The method of claim 12, wherein an electronegativity of the second constituent atom is higher than an electronegativity of the first constituent atom.

16. The method of claim 14, wherein in reacting the first substance and the polymer, the first metal atom is inserted between the silicon atom and the hydrogen atom.

17. A method for manufacturing a compound from a raw material by reduction reaction, oxidation reaction, hydrometalation, carbon-carbon bond-forming reaction or carbon-nitrogen bond-forming reaction using the catalyst according to claim 1 to obtain the compound.

* * * * *